US012329852B2

(12) United States Patent
Wong et al.

(10) Patent No.: US 12,329,852 B2
(45) Date of Patent: Jun. 17, 2025

(54) SUSTAINED-RELEASE 9-CIS RETINOIC ACID IMPLANTABLE DRUG DELIVERY PELLETS FOR THE PREVENTION OF POSTSURGICAL EDEMA AND LYMPHEDEMA

(71) Applicant: UNIVERSITY OF SOUTHERN CALIFORNIA, Los Angeles, CA (US)

(72) Inventors: Alex K. Wong, Los Angeles, CA (US); Young-Kwon Hong, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 278 days.

(21) Appl. No.: 17/950,400

(22) Filed: Sep. 22, 2022

(65) Prior Publication Data

US 2023/0042722 A1 Feb. 9, 2023

Related U.S. Application Data

(62) Division of application No. 16/857,927, filed on Apr. 24, 2020, now Pat. No. 11,484,496.

(60) Provisional application No. 62/838,253, filed on Apr. 24, 2019.

(51) Int. Cl.
*A61K 9/00* (2006.01)
*A61K 31/203* (2006.01)
*A61K 47/06* (2006.01)

(52) U.S. Cl.
CPC .......... *A61K 9/0024* (2013.01); *A61K 31/203* (2013.01); *A61K 47/06* (2013.01)

(58) Field of Classification Search
CPC ..... A61K 9/0024; A61K 31/203; A62K 47/06
See application file for complete search history.

(56) References Cited

PUBLICATIONS

Choi et al, 9-Cis Retinoic Acid Promotes Lymphangiogenesis and Enhances Lymphatic Vessel Regeneration, Circulation. (Year: 2012).*
Bramos, A. et al., "Prevention of Postsurgical Lymphedema by 9-cis Retinoic Acid," Annals of Surgery, v. 264, n. 2, 2016, pp. 353-361.
Choi, I. et al., "9-Cis Retinoic Acid Promotes Lymphangiogenesis and Enhances Lymphatic Vessel Regeneration: Therapeutic Implications of 9-Cis Retinoic Acid for Secondary Lymphedema," Circulation (published by the American Heart Assn), 2012, 28 pgs.
Daneshgaran, G. et al., "Prevention of postsurgical lymphedema via immediate delivery of sustained-release 9-cis retinoic acid to the lymphedenectomy site," J. of Surgical Oncology, 2019, pp. 1-9.
Non-Final Office Action dated Jan. 18, 22 for U.S. Appl. No. 16/857,927, 11 pgs.

* cited by examiner

*Primary Examiner* — Carlos A Azpuru
(74) *Attorney, Agent, or Firm* — Brooks Kushman P.C.

(57) ABSTRACT

A method of treating post-surgical edema includes a step of administering an effective amount of a pharmaceutical composition to a subject identified a risk of post-surgical edema. The pharmaceutic composition include a retinoic acid component selected from the group consisting of 9-cis retinoic acid, geometric isomers of 9-cis retinoic acid, metabolites of 9-cis retinoic acid, substituted derivatives thereof, and combinations thereof. An implantable pellet including the retinoic acid component is also provided.

26 Claims, 22 Drawing Sheets
(14 of 22 Drawing Sheet(s) Filed in Color)

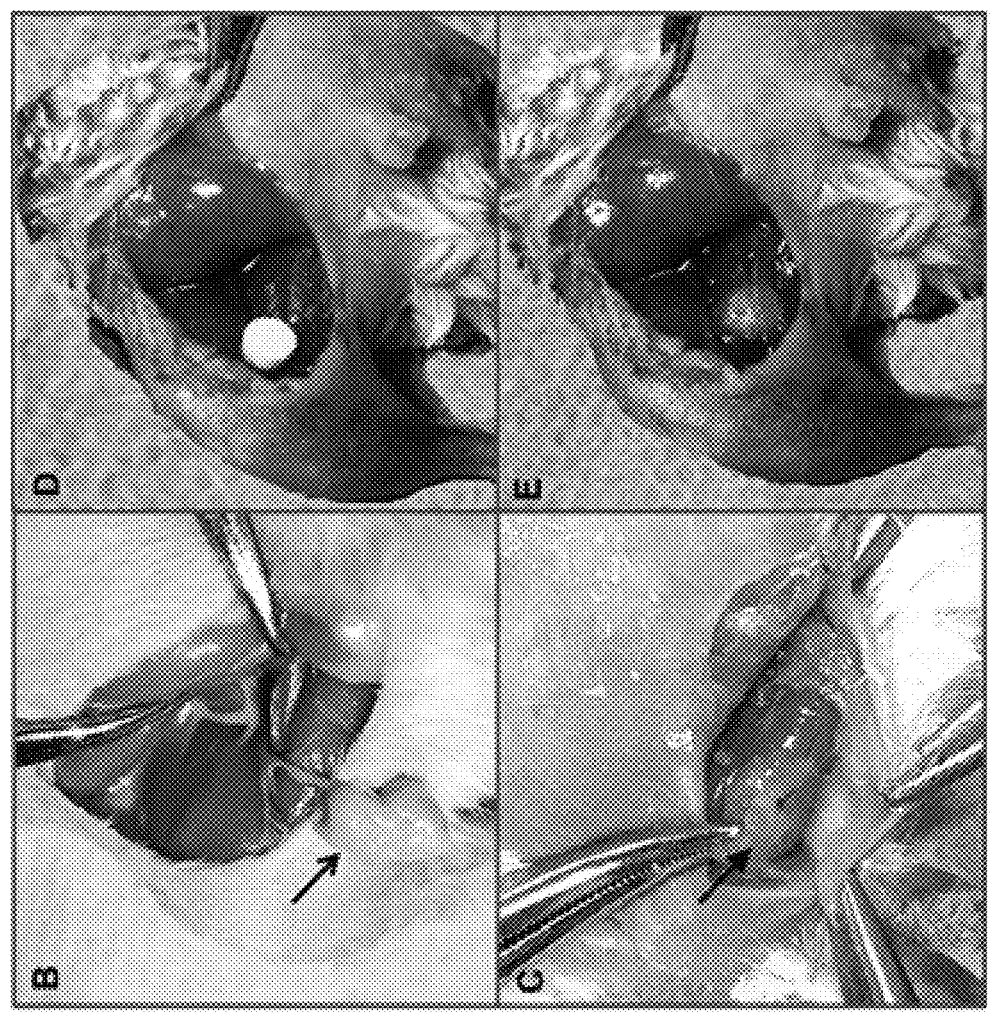
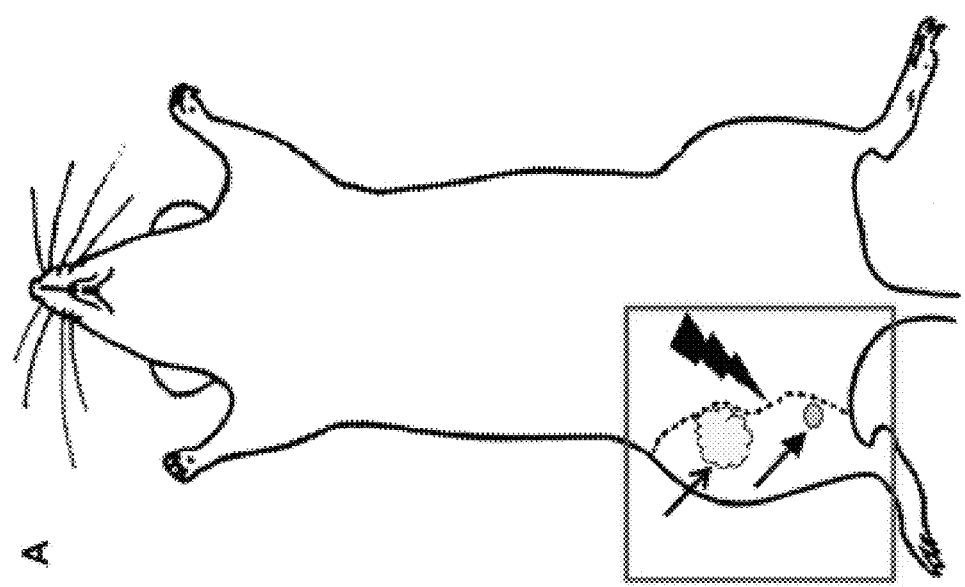

|  | 9-cis Retinoic Acid | | | | |
| --- | --- | --- | --- | --- | --- |
|  | Control | 7 Day | 14 Day | 45 Day | Delay |
| Percent Increase in Tail Volume (at day 42) | 93.67% | 74.27% | 57.65% | 59.93% | 53.04% |
| Dermal Thickness ($\mu m$) | 679.5 | 616.6 | 352.4 | 525.2 | 502 |
| Epidermal Thickness ($\mu m$) | 153.9 | 109.2 | 52.07 | 83.14 | 73.51 |
| ICG Clearance (At 48 hours) | -39.68% | -41.91% | -76.69% | -74.72% | -76.6% |
| Tail Lymphatic Density (Vessels/$\mu m^2$) | $2.977 \times 10^{-5}$ | $4.954 \times 10^{-5}$ | $7.821 \times 10^{-5}$ | $8.754 \times 10^{-5}$ | $5.814 \times 10^{-5}$ |

Table 1. Comparisons of mean values between vehicle treated controls to 9-cis Retinoic Acid treated animals.

*Fig. 12A*

|  | 9-cis Retinoic Acid | | | |
| --- | --- | --- | --- | --- |
|  | 7 Day | 14 Day | 45 Day | Delay |
| Percent Increase in Tail Volume (at day 42) | - | ↓ | ↓↓↓ | ↓↓ |
| Dermal Thickness ($\mu m$) | - | ↓↓↓ | ↓↓ | ↓↓ |
| Epidermal Thickness ($\mu m$) | ↓↓ | ↓↓↓ | ↓↓↓ | ↓↓↓ |
| ICG Clearance (At 48 hours) | - | ↑↑↑ | ↑↑↑ | ↑↑↑ |
| Tail Lymphatic Density (Vessels/$\mu m^2$) | - | ↑ | ↑↑ | - |

↑/↓: Trending towards significance
↑↑/↓↓: Significant at p-value of at least 0.05
↑↑↑/↓↓↓: Significant at p-value of at least 0.01
-: no statistical difference versus the control group;
* Direction of the arrow signifies whether the observed mean is greater than or less than the control mean.

Table 2. Summary of statistical analysis comparing vehicle treated controls to 9-cis Retinoic Acid treated animals.

*Fig. 12B*

SUSTAINED-RELEASE 9-CIS RETINOIC ACID IMPLANTABLE DRUG DELIVERY PELLETS FOR THE PREVENTION OF POSTSURGICAL EDEMA AND LYMPHEDEMA

CROSS-REFERENCE TO RELATED APPLICATIONS

This application is a divisional of U.S. application Ser. No. 16/857,927 filed Apr. 24 2020, which claims the benefit of U.S. provisional application Ser. No. 62/838,253 filed Apr. 24, 2019, the disclosures of which are hereby incorporated in their entirety by reference herein.

STATEMENT REGARDING FEDERALLY SPONSORED RESEARCH OR DEVELOPMENT

This invention was made with government support under HL132110 awarded by the National Institutes of Health. The government has certain rights in the invention.

TECHNICAL FIELD

In at least one aspect, the present invention relates to compositions and methods for treating postsurgical edema and in particular, postsurgical lymphedema.

BACKGROUND

Lymphedema is a disfiguring disease resulting from injury, infection or congenital malformation of the lymphatic system affecting over 250 million individuals worldwide [1]. The proposed pathogenic mechanism is impaired lymphatic transport capacity resulting in the buildup of fluid, protein and fibroadipose tissue in the interstitial space, causing progressive enlargement of the affected body part. Depending on the location of injury, lymphedema can affect the upper extremity, lower extremity, genitalia, abdomen, or head and neck. Primary lymphedema is rare, affecting 1:6,000-10,000 live births due to inborn defects of lymphangiogenesis [2]. Secondary lymphedema is more common and results in a significant disease burden, particularly for the cancer population. In the US, secondary lymphedema affects over 5 million cancer survivors and is most often caused by direct lymphatic injury during the resection or irradiation of solid organ tumors, including breast, gynecologic and lower extremity malignancies [1].

Unfortunately, no curative therapy exists for lymphedema. Symptoms of this progressive disease are variable but can include pain, heaviness, disfigurement, impaired ambulation or activities of daily living, increased risk for infection and wound breakdown, and risk for malignant transformation. The mainstay of lymphedema therapy consists of conservative management in the form of combined decongestive therapy (CDT). The four elements of CDT are manual lymphatic drainage, compression bandaging, exercise and skin care. Conservative management only results in symptomatic relief, is time-consuming and costly, contributing to poor long-term patient adherence [3]. For this reason, advances in the surgical and pharmacologic management of lymphedema have recently garnered scientific interest. New microsurgical procedures, such as vascularized lymph node transfer (VLNT) and lymphaticovenous bypass (LVB), aim to redirect obstructed lymphatic flow into the venous circulation to decongest the affected body part. More extreme debulking procedures, which resect subcutaneous and fibroadipose tissue and cover the resulting defect with skin grafts, are used for patients with extensive tissue fibrosis characteristic of end-stage lymphedema [4].

In an effort to explore nonsurgical options for lymphedema management, current research is exploring the use of drugs with pro-lymphangiogenic properties. Several growth factors have already been shown to stimulate lymphangiogenesis in animal models, such as VEGF-C and VEGF-D [5-8]. However, these drugs have been linked to the promotion of tumor metastasis, making their use relatively contraindicated in patients with a history of cancer, which comprise a significant proportion of lymphedema patients in the US [9-11]. We have shown that a number of retinoic acid derivatives, including 9-cis retinoic acid (9-cis RA) stimulates lymphangiogenesis without promoting tumor metastasis. Further, we have revealed significantly increased lymphatic endothelial cell proliferation, migration and vessel formation when treated with 9-cis RA in vitro. Animal studies have corroborated these findings by demonstrating increased lymphatic vessel density and function in vivo [12,13].

Importantly, unlike the pro-lymphangiogenic growth factors VEGF-C and VEGF-D, 9-cis RA demonstrates a favorable risk profile in patients with a history of cancer since the latter is not a growth factor. It has been FDA-approved in topical form for Kaposi sarcoma of the skin and chronic hand eczema. We have shown that systemic administration of 9-cis RA in the form of daily intraperitoneal injections prevents experimental lymphedema.

Accordingly, there is a need for improved methods and compositions for treating lymphedema, and in particular, post-surgical lymphedema.

SUMMARY

In at least one aspect, the pro-lymphangiogenic effects of 9-cis RA contained within an implantable, single-use pellet for sustained drug delivery in a clinically relevant mouse lymphedema model are investigated. Data from this study set the stage for the use of 9-cis RA pellets in future human trials and aid in the development of a novel pharmacologic agent for the prevention of postsurgical lymphedema.

In another aspect, a method of treating post-surgical edema, and in particular post-surgical lymphedema is provided. The method includes a step of administering an effective amount of a pharmaceutical composition to a subject identified a risk of post-surgical edema. The pharmaceutical composition includes a retinoic acid component selected from the group consisting of 9-cis retinoic acid, geometric isomers of 9-cis retinoic acid, metabolites of 9-cis retinoic acid, substituted derivatives thereof, and combinations thereof.

In still another aspect, an implantable pharmaceutical composition for treating lymphedema and in particular, post-surgical lymphedema is provided. The composition includes a carrier and a retinoic acid component dispersed within the carrier in an effective amount to treat edema (e.g., post-surgical lymphedema, general post-surgical edema). The retinoic acid component is a retinoic acid component selected from the group consisting of 9-cis retinoic acid, geometric isomers of 9-cis retinoic acid, metabolites of 9-cis retinoic acid, substituted derivatives thereof, and combinations thereof Characteristically, the pharmaceutical composition is formed into an implantable pellet.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a further understanding of the nature, objects, and advantages of the present disclosure, reference should be had to the following detailed description, read in conjunction with the following drawings, wherein like reference numerals denote like elements and wherein:

FIGS. 1A, 1B, 1C, 1D, and 1E: Schematic of the hind limb lymphadenectomy model. (A) To induce hind limb lymphedema in mice, the inguinal fat pad (in yellow, indicated by the open arrow) and the popliteal lymph node (in green, indicated by the closed arrow) were surgically dissected. A circumferential skin incision was then made around the thigh along the dotted line, followed by hind limb irradiation. The red square indicates the field of view for images B-E. (B) Intraoperative image identifying the inguinal fat pad containing the inguinal lymphatics (indicated by the open arrow), supplied by the superficial epigastric vessels branching off the femoral vessels. (C) Intraoperative image identifying the popliteal lymph node located within the inferior pole of the adductor thigh muscles (indicated by the closed arrow). (D) Intraoperative image of the implantable pellet placed in situ within the surgical wound. (E) Intraoperative image of the implantable pellet sutured to the fibers of the adductor thigh muscles.

FIGS. 12A and 12B: (A) Table 1. Comparisons of mean values between vehicle treated controls to 9-cis retinoic acid. (B) Table 2. Summary of statistical analysis comparing vehicle treated controls to 9-cis retinoic acid treated animals.

DETAILED DESCRIPTION

Figure 2:
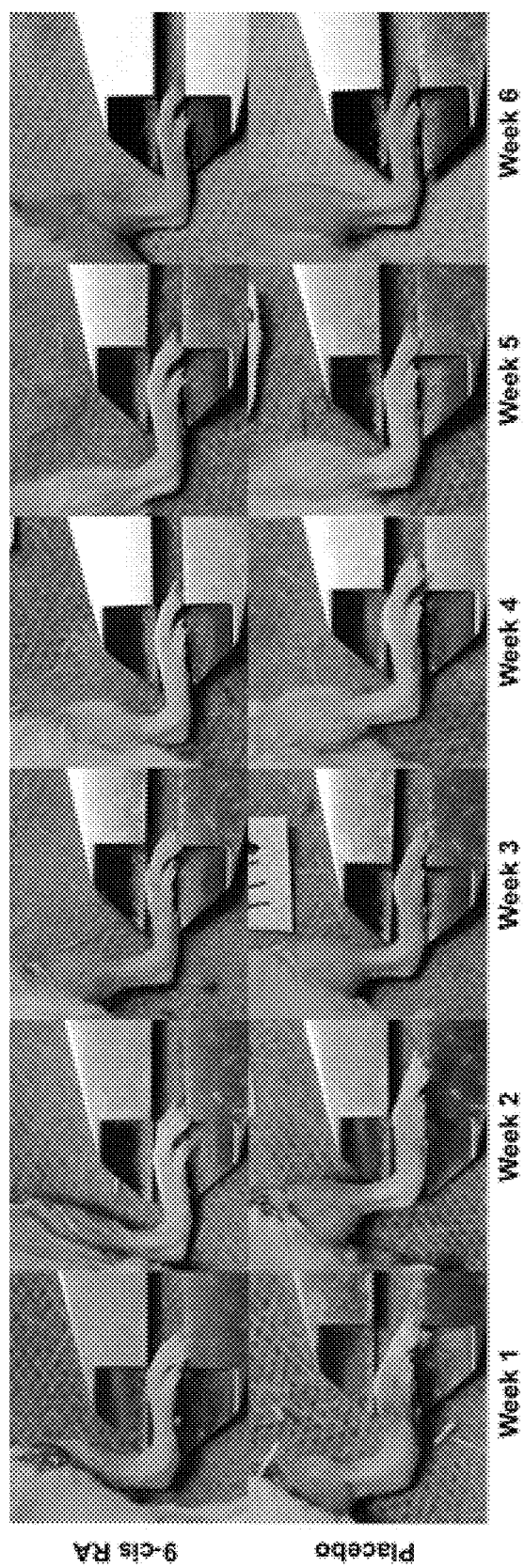
FIG. 2: Representative paw images after inducing hind limb lymphedema in treatment and placebo groups. Compared to control animals receiving placebo, the 9-cis RA group showed consistently less paw swelling as measured by electronic calipers. Subset of data used to plot FIG. 2.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: all R groups (e.g. $R_i$ where i is an integer) include hydrogen, alkyl, lower alkyl, $C_{1-6}$ alkyl, $C_{6-10}$ aryl, $C_{6-10}$ heteroaryl, $—NO_2$, $—NH_2$, —N(R'R"), —N(R'R"R''')$^+$L$^-$, Cl, F, Br, $—CF_3$, $—CCl_3$, —CN, $—SO_3H$, $—PO_3H_2$, —COOH, $—CO_2R'$, —COR', —CHO, —OH, —OR', —O$^-$M$^+$, -SO$_3^-$M$^+$, —PO$_3^-$M$^+$, —COO$^-$M$^+$, $—CF_2H$, $—CF_2R'$, $—CFH_2$, and —CFR'R" where R', R" and R''' are $C_{1-10}$ alkyl or $C_{6-18}$ aryl groups; single letters (e.g., "n" or "o") are 1, 2, 3, 4, or 5; in the compounds disclosed herein a CH bond can be substituted with alkyl, lower alkyl, $C_{1-6}$ alkyl, $C_{6-10}$ aryl, $C_{6-10}$ heteroaryl, $—NO_2$, $—NH_2$, —N(R'R"), —N(R'R"R''')$^+$L$^-$, Cl, F, Br, $—CF_3$, $—CCl_3$, —CN, $—SO_3H$, $—PO_3H_2$, —COOH, $—CO_2R'$, —COR', —CHO, —OH, —OR', —O$^-$M$^+$, —SO$_3^-$M$^+$, —PO$_3^-$M$^+$, —COO$^-$M$^+$, $—CF_2H$, $—CF_2R'$, $—CFH_2$, and —CFR'R" where R', R" and R''' are $C_{1-10}$ alkyl or $C_{6-18}$ aryl groups; percent, "parts of," and ratio values are by weight; the term "polymer" includes "oligomer," "copolymer," "terpolymer," and the like; molecular weights provided for any polymers refers to weight average molecular weight unless otherwise indicated; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

As used herein, the term "about" means that the amount or value in question may be the specific value designated or some other value in its neighborhood. Generally, the term "about" denoting a certain value is intended to denote a range within +/−5% of the value. As one example, the phrase "about 100" denotes a range of 10 0+/−5, i.e. the range from 95 to 105. Generally, when the term "about" is used, it can be expected that similar results or effects according to the invention can be obtained within a range of +/−5% of the indicated value.

As used herein, the ern "and/oi" means that either all or only one of the elements of said group may be present. For example, "A and/or B" shall mean "only A, or only B, or both A and B". In the case of "only A", the term also covers the possibility that B is absent, i.e. "only A, but not B".

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits. In the specific examples set forth herein, concentrations, temperature, and reaction conditions (e.g. pressure, pH, etc.) can be practiced with plus or minus 50 percent of the values indicated rounded to three significant figures. In a refinement, concentrations, temperature, and reaction conditions (e.g., pressure, pH, etc.) can be practiced with plus or minus 30 percent of the values indicated rounded to three significant figures of the value provided in the examples. In another refinement, concentrations, temperature, and reaction conditions (e.g., pH, etc.) can be practiced with plus or minus 10 percent of the values indicated rounded to three significant figures of the value provided in the examples.

Throughout this application, where publications are referenced, the disclosures of these publications in their entireties are hereby incorporated by reference into this application to more fully describe the state of the art to which this invention pertains.

The term "subject" refers to a human or animal, including all mammals such as primates (particularly higher primates), sheep, dog, rodents (e.g., mouse or rat), guinea pig, horse, goat, pig, cat, rabbit, and cow.

The term "excipient" refers to any component or matiral of a pharmaceutical composition that is not 9-cis retinoic acid.

Abbreviation:
"9-cis RA" means 9-cis retinoic acid.
"AST" means aspartate aminotransferase.
"ALT" means alanine transaminase.
"BUN" means blood urea nitrogen.
"CDT" means combined decongestive therapy.
"RA" means retinoic acid.

In an embodiment, a method of treating post-surgical edema and in particular post-surgical lymphedema with a pharmaceutical composition set forth above is provided. The pharmaceutical composition includes a retinoic acid component selected from the group consisting of 9-cis retinoic acid, geometric isomers of 9-cis retinoic acid (e.g., the all trans isomer), metabolites of 9-cis retinoic acid, substituted derivatives thereof, and combinations thereof. Formula 1 provides the formula for 9-cis retinoic acid:

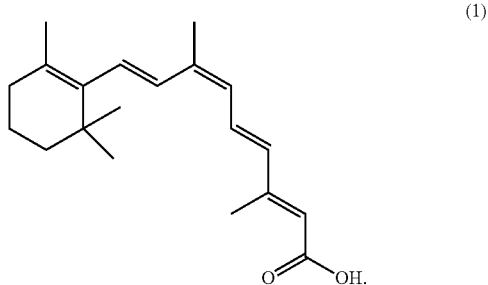 [SMILES: CC1=C(/C=C/C(C)=C\C=C\C(C)=C\C(=O)O)C(C)(C)CCC1]

(1)

In a variation, the compound having formula 1 can be optionally substituted by one or more of alkyl, lower alkyl, $C_{1-6}$ alkyl, $C_{6-10}$ aryl, $C_{6-10}$ heteroaryl, $-NO_2$, $-NH_2$, $-N(R'R'')$, $-N(R'R''R''')^+L^-$, Cl, F, Br, $-CF_3$, $-CCl_3$, $-CN$, $-SO_3H$, $-PO_3H_2$, $-COOH$, $-CO_2R'$, $-COR'$, $-CHO$, $-OH$, $-OR'$, $-O^-M^+$, $-SO_3^-M^+$, $-PO_3^-M^+$, $-COO^-M^+$, $-CF_2H$, $-CF_2R'$, $-CFH_2$, and $-CFR'R''$ where R', R'' and R''' are $C_{1-10}$ alkyl or $C_{6-18}$ aryl groups.

The method includes a step of identifying a subject undergoing surgery that is at risk for edema, and in particular lymphedema. An effective amount of the pharmaceutical composition is administered to the subject. The pharmaceutical composition can be administered by any number of methods know to those skilled in the pharmaceutical art. Examples include, but are not limited to, oral (e.g., sustained release, enteric coated, sub lingual), intravenously (IV), implant/depot, liposomal, intranasal, topical, rectal, transdermal patch, parenteral (e.g., injection), and the like. In a refinement, the retinoic acid component (e.g., 9-cis-retinoic acid) is administered by implanting an implantable pellet into the subject during or after surgery. Characteristically the implantable pellet includes a carrier and the retinoic acid component dispersed within the carrier in an effective amount to treat postsurgical lymphedema. Additional details of the implantable pellet are set forth below with respect to the description of the implantable pharmaceutical composition. For all methods of delivery, a useful dosage for the retinoic acid component is from about 0.001 mg to 50 mg per kg of subject weight. In a refinement, a useful dosage for the retinoic acid component is from about 0.001 mg to 30 mg per kg of subject weight. In another refinement, a useful dosage for the retinoic acid component is from about 1 mg to 30 mg per kg of subject weight. In some refinements, the dosage is administered over a time period from 15 to 90 days. In a further refinement, the dosage is administered over a time period from 15 to 60 days. In a further refinement, the dosage is administered over a time period from 15 to 45 days.

Advantageously, the method of the present embodiment can relieve post-surgical edema and in particular lymphedema and/or general edema after surgery. Examples of situation in which edema can be alleviated include, but are not limited to, bowel edema, brain swelling after neurosurgery, facial surgery (fracture repair, cosmetic face/eye lifts, rhinoplasty), hand and lower extremity surgery, and the like.

Typically, the pharmaceutical composition will include one or more common diluents, excipients, and other carriers routinely utilized in pharmaceutical compositions. Examples of such components include but are not limited to, polyols such as glycerin, ethylene glycol, sorbitol 70; mono- and difatty acid esters of ethylene glycol. Additional examples of carriers and/or excipients and/or diluents include inorganic salts, cholesterol, lactose, celluloses, phosphates, and stearates. In a refinement, examples of carriers and/or excipients and/or diluents include, but are not limited to, starches and sugars such as corn starch, sucrose, lactose, and the like, can be utilized for solid preparations. Such solid formulations can be in the form of tablets, pills, capsules, troches, and the like. Additional examples of examples of carriers and/or excipients and/or diluents include, but are not limited to, monosaccharides, disaccharides, polyhydric alcohols, and mixtures thereof. More specific examples of diluents include dextrose, lactose monohydrate, anhydrous lactose, sucrose, mannitol, spray-dried mannitol, xylitol, sorbitol and combinations thereof.

In another variation, the 9-cis RA is provided as a pharmaceutical composition for oral administration. In one refinement, the 9-cis RA can be provided as a tablet, pill, or capsule in which the 9-cis RA is combined with a solid carrier that includes one ore more optional excipients and/or diluents as set forth above. In another refinement, the 9-cis RA as a liquid formulation in which the 9-cis RA is combined with a liquid carrier. The liquid carrier can include water, alcohol (e.g., ethanol), oils (e.g., vegetable oils), or combinations thereof. Detail of the dosage of 9-cis RA in this variation are the same as set forth above.

In another embodiment, an implantable pharmaceutical composition for treating post-surgical edema and in particular, post-surgical lymphedema is provided. The composition includes a carrier and a retinoic acid component (e.g., 9-cis retinoic acid) dispersed within the carrier in an effective amount to treat edema (e.g., post-surgical lymphedema, general edema following surgery, and the like). In a variation, the retinoic acid component is selected from the group consisting of 9-cis retinoic acid, geometric isomers of 9-cis retinoic acid, metabolites of 9-cis retinoic acid, substituted derivatives thereof, and combinations thereof. Characteristically, the pharmaceutical composition is formed into an implantable pellet. Therefore, sometimes the implantable pharmaceutical composition is referred to as the "implantable pellet." In a variation, the retinoic acid component (e.g., 9-cis retinoic acid) is present in an amount of 0.001 to 30 milligrams in the implantable pellet. In a refinement, the retinoic acid component (e.g., 9-cis retinoic acid) is present in an amount of 0.001 to 10 milligrams per kg of subject weight in the implantable pellet.

Typically, the carrier is at least partially biodegradable. Therefore, the carrier can advantageously be a biodegradable matrix that effectively and continuously releases 9-cis retinoic acid after implantation in a subject over (e.g., for an implantable pellet). Typically, the carrier is designed for about 15 to 90 days of treatment with a single pellet. In a refinement, the carrier is designed for about 15 to 60 days of treatment with a single pellet. In a further refinement, the carrier is designed for about 15 to 45 days of treatment with a single pellet. In another refinement, at least 90 percent of the 9-cis retinoic acid is released into the subject after 60 days post implantation. In a refinement, at least 90 percent of the 9-cis retinoic acid is released into the subject after 30 days post implantation.

In some variations, a sustained release formulation of the 9-cis retinoic acid or derivatives thereof is provided. In this context, a sustained release formulation is a formulation that is designed to release the 9-cis RA at a predetermined rate in order to maintain a constant or near constant drug concentration for a specific period of time. In a refinement, the sustained release formulation include a matrix system that is mixed with the 9-cis RA. This matrix allows the 9-cis RA to slowly released. Examples of matrices include, but are not limited to, hydrophobic matrices, lipid matrices, hydrophilic matrices, biodegradable matrices, and mineral matrices. More specific examples of matrices include, but are not limited to, cellulose derivatives, non-cellulose natural, and polymers of acrylic acid, lipid matrices uses wax or similar materials. Biodegradable matrices typically include unstable, linked monomers that erode by biological compounds (e.g., enzymes and proteins). In another refinement, the sustained release formulation is a diffusion system in which the 9-cis RA diffuses across a barrier polymer. In another refinement, the sustained release formulation is an osmotic controlled-release oral delivery system. In this refinement, the 9-cis RA is formed into a tablet that is coated with an outer membrane. Holes are formed in the outer membrane (e.g., drilled therein) does that the 9-cis RA can be release by osmotic pressure.

Additional details of embodiments set forth herein are found in Giulia Daneshgaran et al. Sustained-Release 9-cis Retinoic Acid Pellets for the Prevention of Postsurgical Lymphedema, J Surg Oncol. 2020; 121:100-108 (25 Jun. 2019) (doi.org/10.1002/jso.25587); the entire disclosure of which is hereby incorporated by reference in its entirety.

The following examples illustrate the various embodiments of the present invention. Those skilled in the art will recognize many variations that are within the spirit of the present invention and scope of the claims.

1. Implantable Pellet Experiments
Materials and Methods
Animals

All experiments were performed in accordance with the statutes from *The Guide for the Care and Use of Laboratory Animals* (National Research Council, 8th ed, 2011), the Animal Welfare Act, and other Federal regulations. The was approved by the University of Southern California Institutional Animal Care and Use Committee. Male and female Prox-1 green fluorescent protein (GFP) transgenic mice, 12-16 weeks old, weighing 20-30 g were bred within the University of Southern California animal facility. This GFP-expressing lymphatic reporter mouse was used because it conveniently allowed for the visualization of lymphatic vessels and other Prox1-expressing tissue under fluorescence microscopy, and facilitated the immunohistochemical staining of lymphatic vessels using anti-GFP primary antibody [13,14].

Hind Limb Lymphedema Model

Under isoflurane-inhaled anesthesia, the lymphatic injury protocol was used on all experimental mice to induce hind limb lymphedema. This consisted of hind limb lymph node dissection followed by adjuvant radiation therapy. Using a dissecting microscope, a circumferential intradermal incision was made around the thigh, after which the ipsilateral inguinal fat pad, containing the inguinal lymph nodes, and ipsilateral popliteal lymph node were removed, as previously described [13]. Visualization of the inguinal and popliteal lymphatics was facilitated by the injection of methylene blue dye on the dorsum of the paw and by the use of a green fluorescent microscope. Skin sutures were placed in 7-8 mm gaps to reinforce discontinuity of dermal lymphatics. The surgical area was then irradiated using a clinically relevant dose of 27.5 Gy radiation delivered by an XRad 320 device over a period of 5 days (550 cGy per day), which is the human equivalent dose for mouse.

Experimental Design

Using the Prox-1 GFP-expressing lymphatics reporter mouse hind limb lymphedema model, eighteen (18) mice were divided into two groups: (1) the treatment group received implantable pellets containing 9-cis RA, 2) the control group received implantable placebo pellets containing inactive compound. Pellets were placed within the surgical wound intraoperatively and sutured in place to the adductor muscles of the thigh. Treatment pellets were custom-manufactured by Innovative Research of America (Sarasota, FL) to contain 100 μg of 9-cis RA, released over a period of 30 days using a matrix-driven delivery system. The carrier-binder excipients of the pellet matrix were synthetic and non-toxic, and included cholesterol, lactose, celluloses, phosphates, and stearates. This resulted in a biodegradable matrix that effectively and continuously released the active product in the animal.

Postoperative Measurements

Prior to surgery, all animals were sex-, age-, and weight-matched to eliminate confounding variables. Paw thickness, the primary outcome, was measured weekly using electronic calipers for a total of 6 weeks. Paw thickness was normalized for each animal by calculating percent change relative to the unaffected paw. Hind limbs were photographed using a Nikon D5000 digital SLR flash camera using fixed distances, focal length, background, and positioning.

ICG Lymphography

At postoperative week 6, lymphatic clearance was measured using indocyanine green (ICG) lymphography to compare lymphatic function between the treatment and placebo groups. After inducing anesthesia via isoflurane inhalation, a sub-microliter injection system syringe was used to intradermally inject 2 uL of ICG on the dorsal aspect of the second and fifth paw digits. ICG lymphography images were recorded at 1, 3, 6, 12, 24, 48, 72, 96, and 144 hours post-injection. The fluorescence intensity of the lymphography images was quantified at each post-injection time point using ImageJ pixel intensity analysis (National Institutes of Health, Bethesda, MD).

Histological and Immunohistochemical Analysis

Hematoxylin and Eosin (H&E) staining of mouse paws was performed to document differences in histological architecture of the soft tissues of the paw between treatment and control groups. Immunohistochemistry (IHC) for GFP was performed to visualize lymphatics within the soft tissues of the paw in order to document differences in lymphatic vessel structure and perform a semi-quantitative analysis of lymphatic vessel density.

Statistical Analysis

For all outcomes, statistical analysis was conducted using Student's t-test to compare the means of the treatment and placebo groups at all time points using Prism 8 software (GraphPad Software, Inc., San Diego, CA).

Results
Implantable 9-cis RA Pellets Prevent Postsurgical Hind Limb Lymphedema

Figure 3:
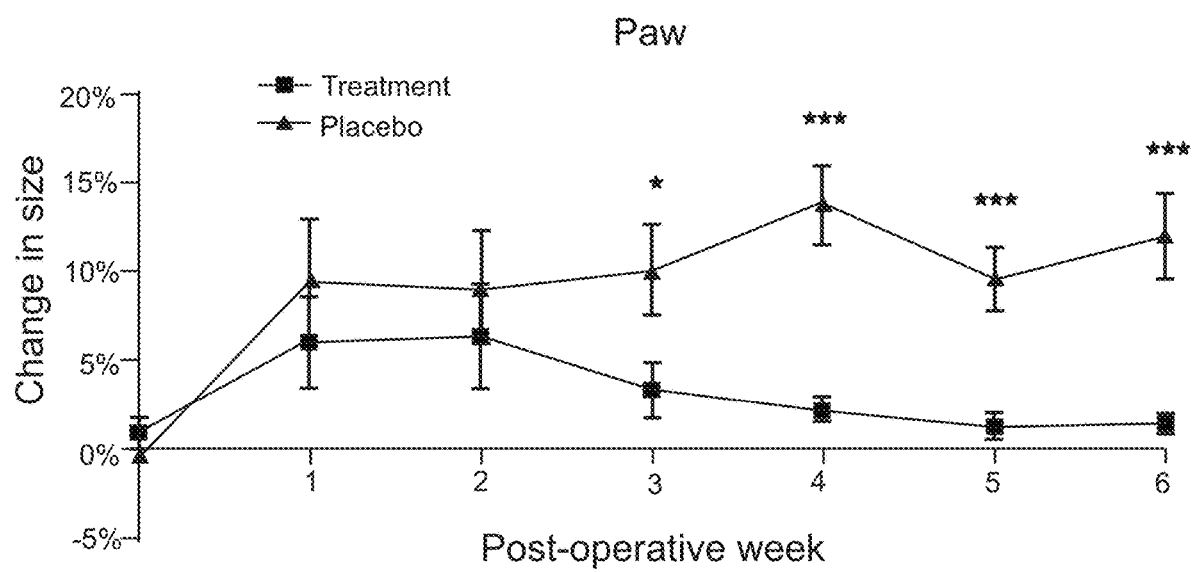
FIG. 3: 9-cis RA decreases paw swelling over time. Compared to control animals, animals treated with 9-cis RA showed significantly reduced paw swelling postoperatively at week 3 (7% mean difference, P=0.04), week 4 (12% mean difference, P=0.0002), week 5 (9% mean difference, P=0.0005), and week 6 (11% mean difference, P=0.0007). Within the treatment group, no significant differences in paw swelling are observed between time points.

Previously, we have shown that daily intraperitoneal injections of 9-cis RA (0.08 mg/kg) prevents postsurgical lymphedema in mice [13]. To test a more clinically feasible route of administration, 9-cis RA was incorporated into an implantable, 30-day sustained-release pellet and placed within the surgical site intraoperatively at the same time that hind limb lymphedema was induced in Prox1-GFP mice (FIGS. 1 A-E). The progression of lymphedema in control and treatment animals was assessed by measuring paw thickness over a period of 6 weeks (FIG. 2). As seen in FIG. 3, animals treated with 9-cis RA pellets showed significantly reduced paw swelling than control animals, beginning on postoperative week 3 and then every week thereafter for the duration of the study. Moreover, intragroup changes in paw size were analyzed over time to assess the degree of lymphedema progression within each group. While the placebo group demonstrated significant increases in paw thickness over time, no significant difference in paw thickness was observed within the treatment group over time. Thus, animals treated with 9-cis RA pellets did not develop a degree of paw swelling that was consistent with lymphedema development.

Implantable 9-cis RA Pellets Increase Lymphatic Clearance

Figure 4:
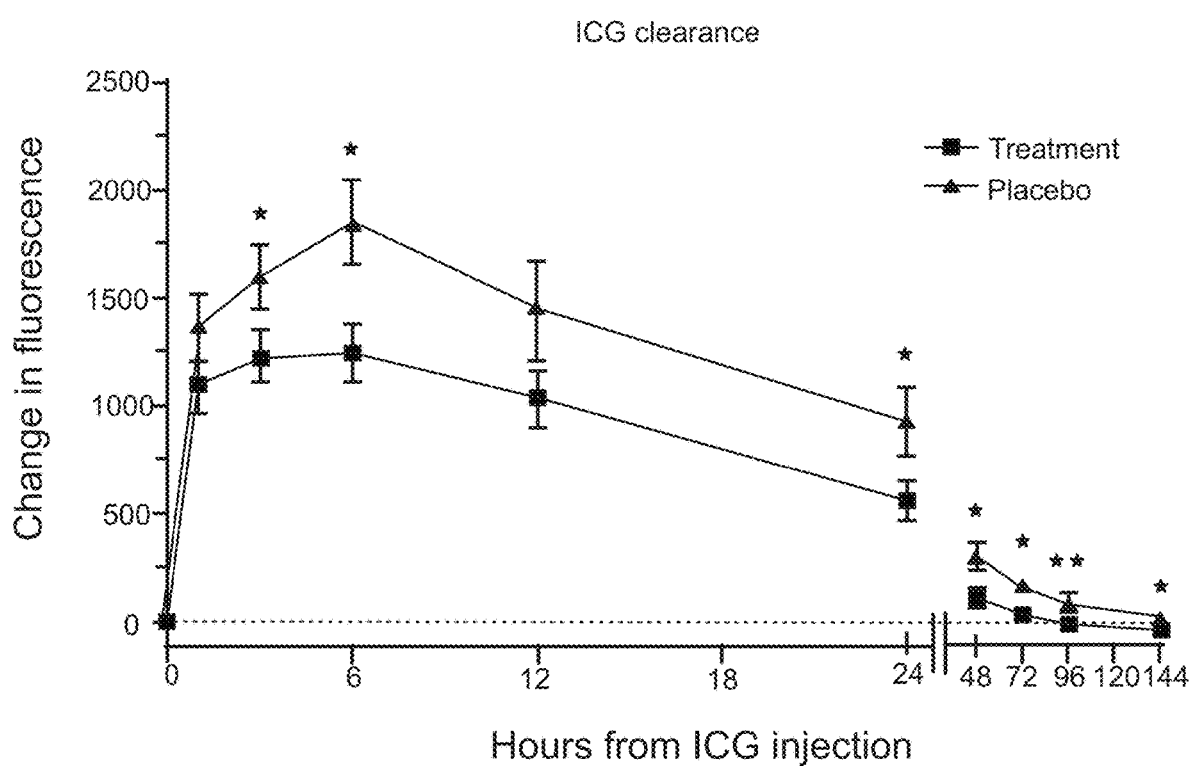
FIG. 4: 9-cis RA results in faster lymphatic clearance. Compared to control animals, animals treated with 9-cis RA showed significantly faster lymphatic drainage as measured by change in ICG fluorescence at 3, 6, 24, 48, 72, 96 and 144 hours following ICG injection (P<0.05).

Indocyanine green (ICG) lymphography is a well-established procedure used in clinics by healthcare providers to visualize lymphatic vessels in real-time for the purposes of diagnosis or preoperative planning. When ICG is injected intradermally, it is preferentially picked up and cleared by the lymphatic system. This imaging modality provides rapid visualization of lymphatic vessels and measures lymphatic clearance, acting as a surrogate for lymphatic function. Using the principles of ICG lymphography, it is hypothesized that the degree of hind limb lymphedema would correlate with degree of lymphatic blockage. Thus, at postoperative week 6 and prior to euthanasia, lymphatic clearance were monitored by quantifying the change in dermal fluorescence of mouse hind limbs injected with ICG. Compared to control animals, animals treated with 9-cis RA revealed significantly faster lymphatic drainage beginning 3 hours after ICG injection and until 144 hours post-injection, when lymphographic analysis was terminated (FIG. 4).

Implantable 9-cis RA Pellets Prevent Epidermal Hyperplasia

Figures 5A, 5B:
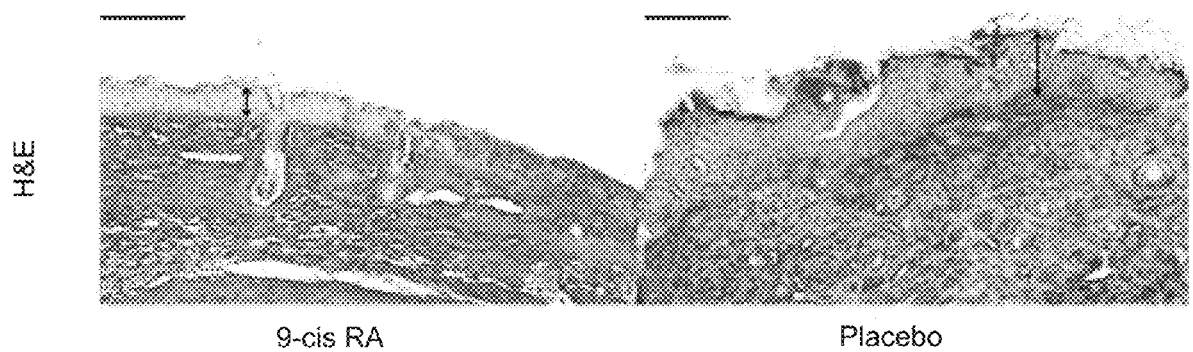
FIGS. 5A, 5B, and 5C: 9-cis RA decreases epidermal hyperplasia on skin histology. (A) H&E stained section of paw skin from treatment mouse. (B) H&E stained section of paw skin from placebo mouse. Horizontal scale bars represent 100 um. Vertical arrows represent Malpighian layer thickness. (C) Animals receiving 9-cis RA pellets showed a 55% decrease in Malpighian layer thickness compared to animals receiving placebo (P=0.04), indicating reduced progression of epidermal hyperplasia in the treatment group.
Figure 5C:
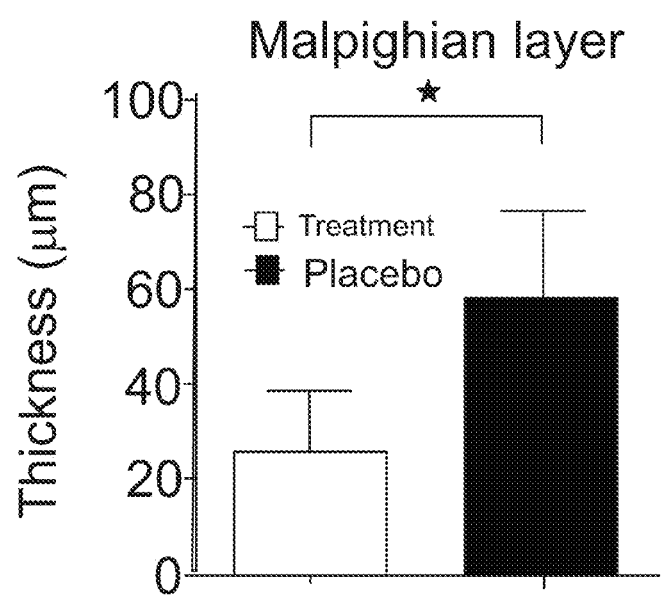

Epidermal hyperplasia is a common histological finding of skin tissue affected by lymphedema. In the present study, epidermal hyperplasia is quantified by measuring the thickness of the Malpighian layer in H&E sections of mouse paw skin. The Malpighian layer consists of the intrinsic stratum spinosum and stratum basale layers of skin. This was specifically measured to exclude the thickness of the stratum corneum on skin analysis, as the stratum corneum can be artificially altered by tissue processing and other environmental factors, thus acting as a confounding variable. As shown in FIGS. 5 A-C, the Malpighian layer was significantly thinner in animals treated with 9-cis RA pellets compared to control animals (55% mean difference, P=0.04). This suggests that 9-cis RA released from implantable pellets prevents epidermal hyperplasia and thus, lymphedema progression, compared to animals receiving placebo.

Discussion

Postsurgical lymphedema commonly occurs in the setting of lymphadenectomy and radiation in the treatment of solid cancers. Its incidence is high in the population of cancer survivors, as it develops in 16-39% of breast cancer patients following axillary lymph node dissection, 20-30% of lower extremity sarcoma and melanoma patients, and 20-49% of patients with gynecological malignancies following ilioinguinal lymph node dissection [15,16]. The extremities are the area most commonly affected by lymphedema. Of the patients with postsurgical lymphedema, approximately 90% have lower extremity lymphedema and 10% have upper extremity lymphedema [17]. The mainstay of lymphedema therapy is achieved through conservative management with variable rates of success, significant healthcare costs and poor patient adherence. Moreover, no curative therapy exists for established disease, which results in significant fibroadipose tissue deposition causing physical deformity and chronic functional deficits. For this reason, early interventions aimed at improving lymphatic function have the greatest potential at limiting disease progression.

Alternative therapies for lymphedema, such as surgical procedures that restore lymphatic flow and pharmacologic agents that promote lymphatic vessel formation, are currently being investigated. Of the more promising pharmacologic agents for lymphedema are members of the VEGF family (VEGF-C and VEGF-D) and 9-cis retinoic acid. The VEGF molecules are contraindicated in the cancer population, as they have been associated with the promotion of tumor metastasis. On the other hand, 9-cis RA is already FDA-approved in the US for other conditions and has been shown to stimulate lymphangiogenesis and lymphatic vessel formation both in vitro and in vivo. To date, 9-cis RA has been tested in animal studies via daily intraperitoneal administration, which is cumbersome and impractical in clinical settings, as it requires daily follow-up over a period of multiple weeks. To facilitate the potential development of 9-cis RA into a form suitable for human use and testing in clinical trials, we developed a novel technique for 9-cis RA administration. Through the intraoperative single-use implantation of a biodegradable pellet containing 100 ug 9-cis RA, we were able to provide sustained drug release over a period of 30 days in our mouse hind limb lymphedema model.

The outcomes investigated in this study were paw size, lymphatic clearance, and epidermal thickness. Paw swelling was used as clinical evidence of distal hind limb lymphedema, lymphatic clearance was used to assess lymphatic vessel function, and epidermal hyperplasia was used as histological evidence of lymphedema. In the treatment group, we observed a significant reduction in paw swelling, increased lymphatic clearance, and reduced epidermal hyperplasia compared to placebo-treated animals. Together, these findings indicate that 9-cis RA contained within a single-use depot pellet drug delivery system has favorable properties in limiting postsurgical lymphedema. Importantly, the maximal difference in paw swelling between the treatment and placebo groups was seen at postoperative week 4 (12% mean difference, P=0.0002). This coincides with the time at which postsurgical changes caused by local mediators of inflammation and edema have subsided. Postoperative week 4 also coincides with the end of the 30-day release of 9-cis RA from the treatment pellets. The fact that a significant difference in paw swelling was still observed until postoperative week 6 suggests that the effects of 9-cis RA in limiting postsurgical lymphedema last beyond the period of known drug release. Thus, 9-cis RA released from our custom-made implantable pellets might have lasting effects in limiting the progression of symptoms of postsurgical lymphedema.

In summary, a clinically feasible method of drug delivery for the management of postsurgical lymphedema is presented. The clinical applicability of an implantable drug-delivery pellet that results in the sustained local release of the pro-lymphangiogenic drug, 9-cis RA, has significant implications to the field of lymphedema. It allows for the convenient administration of 9-cis RA, which, from a patient and provider perspective, would mean fewer follow-up appointments and decreased treatment costs than the previously investigated daily administration of 9-cis RA given intraperitoneally. Moreover, it would facilitate early disease intervention, thus preventing establishment of late-stage lymphedema. Once its safety and efficacy have been investigated in humans using this novel method of administration, 9-cis RA can become the first pharmacologic agent approved for the treatment of secondary postsurgical lymphedema.

2. Injection Experiments
Methods
Animals

All experiments were performed in accordance with the *The Guide for the Care and Use of Laboratory Animals* (National Research Council, 8th ed, 2011) and the Animal Welfare Act. Our protocol was approved by the University of Southern California Institutional Animal Care and Use Committee. Fifty adult BALB/c mice, 12 to 14 weeks old, weighing between 21 and 30 g were purchased from Jackson Laboratories (Jackson, Bar Harbor, ME). Animals were maintained in a temperature and light-controlled environment with ad libitum access to a normal chow diet and water.

Mouse Tail Secondary Lymphedema Model

A previously well described tail model to induce lymphedema was modified in the present experiments. Mice were anesthetized using 2.5% isofluorane, and a 5-mm wide circumferential skin excision was made 20-mm from the base of the tail. Underlying lymphatic vessels were visualized using isosulfan blue and ligated under a dissecting surgical microscope [1, 2, 6]. Daily bacitracin antibiotic ointment was applied to the surgical site to prevent wound infection and desiccation.

Experimental Design

Animals were randomly assigned to one of five groups following surgery: control, 7 days, 14 days, 45 days, and delay. Mice received daily intraperitoneal injections of either 100 µL vehicle solution (90 µL sunflower seed oil/10 µL 100% ethanol) or 0.08 mg/kg 9-cis RA dissolved in 100 µL of vehicle solution [5]. The treatment administered to each group was: (1) control: vehicle for 45 days following surgery, (2) 7 day: 9-cis RA for 7 days, (3) 14 day: 9-cis RA for 14 days, (4) 45 day: 9-cis RA for 45 days, and (5) delay: 9-cis RA for 7 days beginning one week after surgery. Animals with necrotic tails or that developed surgical site infections were sacrificed and excluded from analysis.

Animals were photographed every five days for a 6-week duration, and tail diameter was measured using ImageJ (National Institutes of Health, Bethesda, MD). Measurements were taken at 5-mm intervals from the distal-most edge of the wound for a total of seven measurements per animal for every time point. Total distal tail volume was calculated using the truncated cone formula [8]. Percent change in distal tail volume was recorded, analyzed, and plotted using GraphPad Prism 7 (GraphPad Software, Inc.).

Indocyanine Green Lymphangiography

On Day 45, animals were anesthetized using 2.5% isofluorane, and 5 µL of 2.5 mg/mL indocyanine green (ICG) was injected into the distal end of each animal's tail 15 minutes prior to imaging. The SPY Elite Fluorescence Imaging System (Novadaq Technologies, BC, Canada) was used to capture fluorescent images and heat maps of the tails at 0, 1, 2, 3, 6, 12, 24, and 48 hours following ICG injection. Capture conditions were kept constant throughout the trial. Fluorescent intensity of the tails at each time point was quantified using a previously described method for measuring cell fluorescence in ImageJ [4, 7]. Values were then recorded and plotted using GraphPad Prism 7. Percent change in fluorescent intensity from the peak fluorescent uptake at 6 hours was used to measure ICG clearance.

Tissue Processing and Staining for Histology

Tail specimens were collected on post-operative day 47. Specimens were harvested to include 1 cm proximal and 1 cm distal the wound, then divided to separate proximal and distal portions. Tails were inked to enable proper orientation, fixed in 10% neutral buffered formalin overnight, decalcified in 10% EDTA (pH: 7.3) for 6 days at 4° C., embedded in paraffin, sectioned at 3-5 µm, then stained with hematoxylin and eosin (H&E) or via immunohistochemical techniques. In summary, sections were deparaffinized, underwent antigen retrieval with sodium citrate buffer, incubated overnight with the primary antibody (1:200) at 4° C., washed, incubated with a suitable secondary antibody (1:200), then stained with immPACT DAB Substrate (Vector Laboratories, Inc, Burlingame, CA) and counterstained with Delafield Hematoxylin (Sigma-Aldrich, USA) diluted 1:4. Podoplanin (clone 8.1.1; sc-53533, Santa Cruz Biotechnology, Inc., Dallas, TX) was used to immunohistochemically mark lymphatics in paraffin embedded tail sections.

Bilateral ears of animals were harvested simultaneously with the diaphragm, removed of all hair using depilatory cream and fixed in 4% paraformaldehyde. The ears were then split between the inner and outer layers under a dissecting microscope and the cartilage removed prior to immunoflourescence staining. The whole mounted specimens were subsequently stained with anti-LYVE-1 and anti-CD-31 antibodies after washing with PBS, permeabilizing with 0.5% Triton X-100 (Sigma-Aldrich, USA), and incubated with the primary antibody (1:500) overnight. Green secondary antibodies (1:200 donkey anti-rabbit Alexa Fluor 488, Thermo Fisher Scientific, Canoga Park, CA) were used to stain for LYVE-1.

Histologic Image Quantification

Slides were counterstained with hematoxylin and mounted. All images were obtained with a Keyence BZ-X700 microscope (Itasca, IL) and epidermal and dermal thickness was measured using ImageJ (National Institutes of Health, Betheseda, MD). The thickest part of the epidermis and dermis was measured in 5 high-power fields per section, as previously described. On the immunohistochemically stained slides, podoplanin stained vessels in the dermis and subcutis were quantified in ImageJ. Two high-power fields per section were randomly selected and then analyzed by a blinded reviewer. The reviewer scored the number of podoplanin stained vessels and the area ($mm^2$) of the dermis and subcutaneous tissue in each image. Lymphatic vessel density was calculated from the absolute lymphatic number normalized to the dermal and subcutaneous area measured (number of lymphatics/$mm^2$).[2] For the immunofluorescent stained slides, LYVE-1 stained vessels were quantified with ImageJ, to assess included lymphatic density, lymphatic vessel width, inter-lymphatic vessel distance, branching points, loops and blind-ended sacs.

India Ink Staining of the Diaphragm

On post-operative day 47, each animal was intraperitoneally injected with 5 cc of India Ink which was diluted 2-folds with distilled water. Ten minutes after the injection of India ink, the animal was euthanized and the diaphragms were harvested in their entirety. The specimens were then rinsed with running tap water for 1 minute and mounted on the stage of a dissecting microscope equipped with a digital camera. The whole-mount specimen, exclusive of the central tendon, was then analyzed for the passive lymphatic absorption of India ink utilizing the percent stained area on ImageJ.

Statistics

All statistical analyses were performed with GraphPad Prism 7 (GraphPad Software, Inc.). ANOVA and unpaired Student's t-tests were used to compare treatments against control at each measurement interval.

Results

Effect of Early Withdrawal or Delayed Initiation of 9-cis RA on Lymphedema.

Figure 6A:
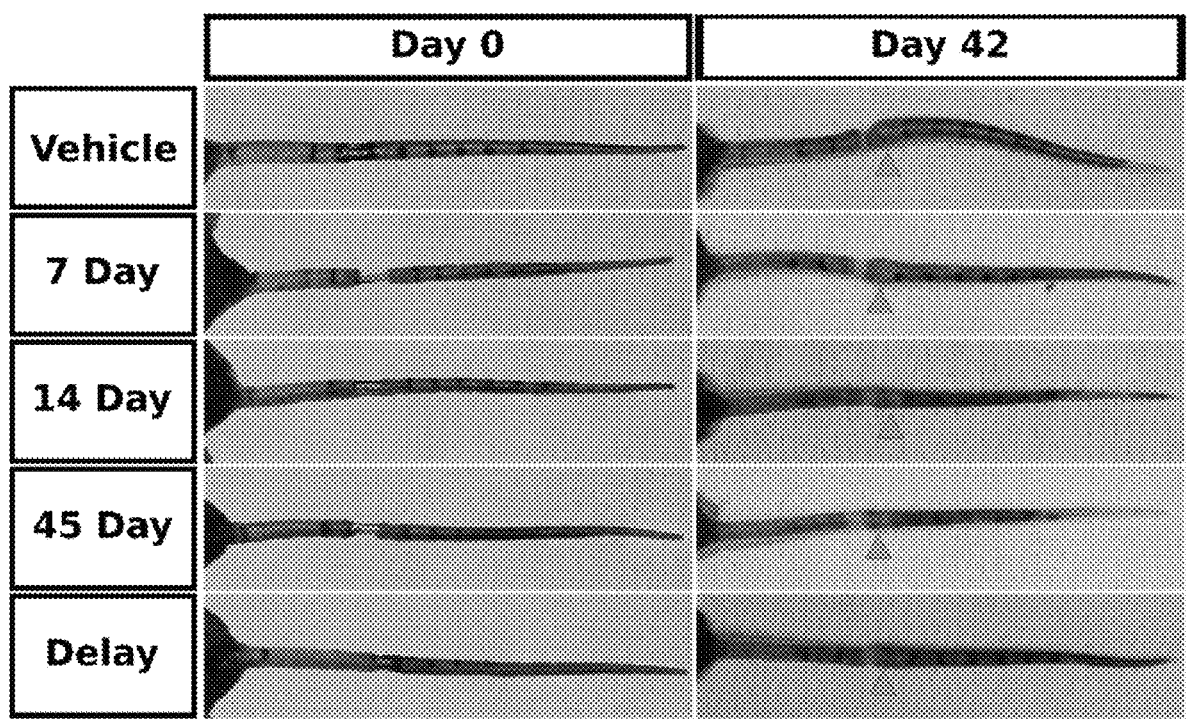
FIGS. 6A and 6B: Effect of 9-cis Retinoic Acid on lymphedema. (A) Representative photos of mouse tails on the day of lymphatic ligation and on the final day of the experiment. Orange arrows indicate location of largest tail circumference on day 42 in each group. (B) Graphical representation of percent change in tail volume from baseline as a function of time. Graph compares increase in tail volume of control group to the 7-day delayed, 7-, 14-, and 45-day groups. Values reported as mean±standard error.
Figure 6B:
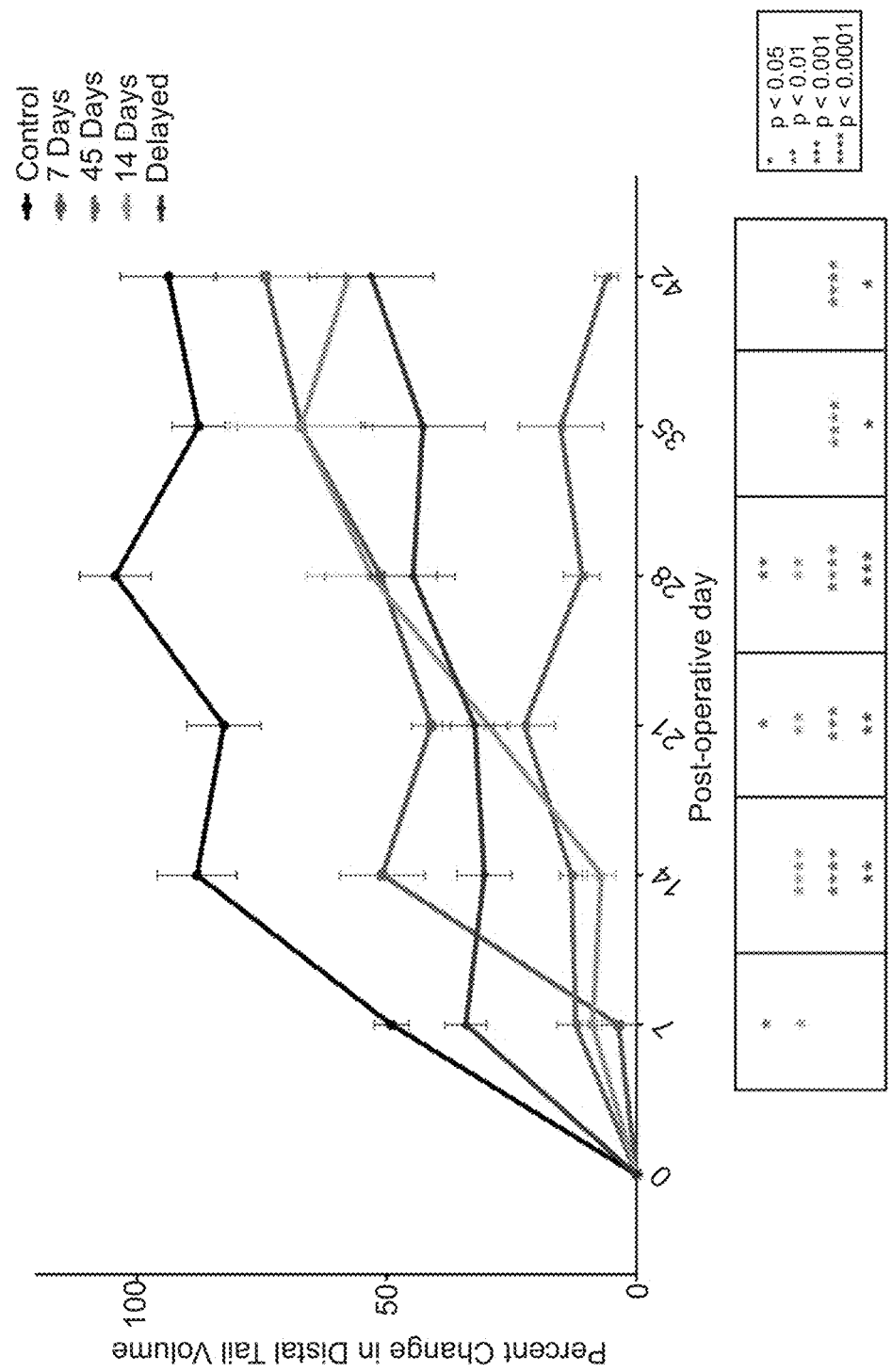

Previously, we demonstrated that daily systemic administration of 9-cis RA (0.08 mg/kg) for 6 weeks (42 days)

significantly prevents development of lymphedema after lymphatic disruption. Although 9-cis RA is a safe FDA approved drug, long term systemic therapy can have unintended side effects. We therefore wished to determine if a limited window of administration was sufficient for 9-cis RA to mitigate lymphedema after surgical injury. We were also interested in whether delayed administration of 9-cis RA could be effective as this may be an important issue relevant to clinical translation (i.e., if a patient undergoes lymphadenectomy and is not started on 9-cis RA immediately post-op, would 9-cis RA be effective if started a week later). To address these questions, we induced lymphedema using an established mouse tail model and randomly assigned them to the following treatment groups: 1) Vehicle (control); 2) 7 days; 3) 14 days; 4) Delayed by 7 days; 5) 42 days. Tail volumes were measured once weekly using the truncated cone formula and tail measurements from pre-marked locations of the mouse tail. Representative images are shown in FIG. 6A. The percent change in tail volumes from pre-surgery were recorded until day 42 for all groups. Animals treated with continuous daily systemic 9 cis-RA treatment had tail volumes that were significantly smaller than the lymphedematous controls. Tail volumes were highly significant beginning on the second week of treatment, and showed a significant difference throughout the entire duration of the experiment. Animals treated for 7- and 14-days showed early differences from the control group, however, approached tail volumes similar to the lymphedematous control group past the 4-week time point. Interestingly, the 7-day delay group showed a statistically significant decrease in tail volumes from day-14 onwards (FIG. 6B).

Figure 7A:
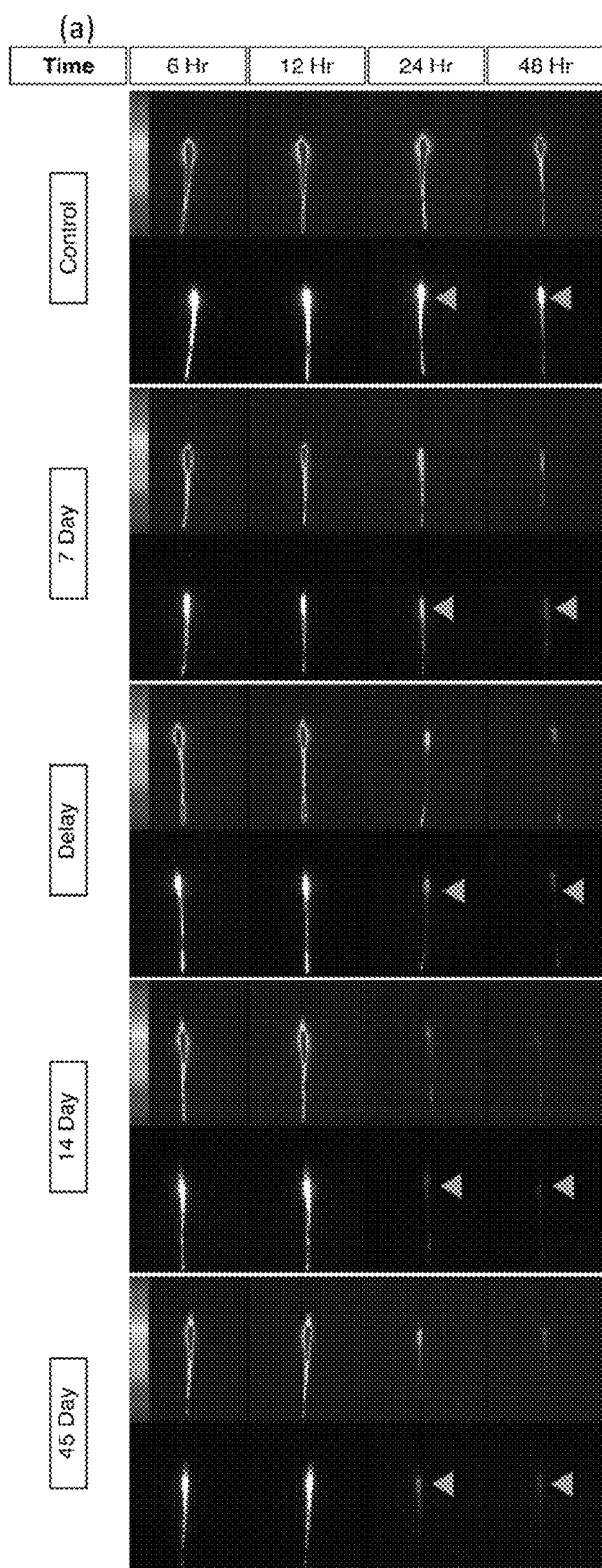
FIGS. 7A and 7B: ICG Lymphangiography. (A) Lymphatic clearance at 6, 12, 24, and 48 hours after injection of ICG measured using ICG lymphangiography. Arrowheads at 24- and 48-hour time points signify change in fluorescent intensity of all group. (B) Graphical representation of ICG clearance in each group represented by the percent change in fluorescence over time. Values reported as mean±standard error.
Figure 7B:
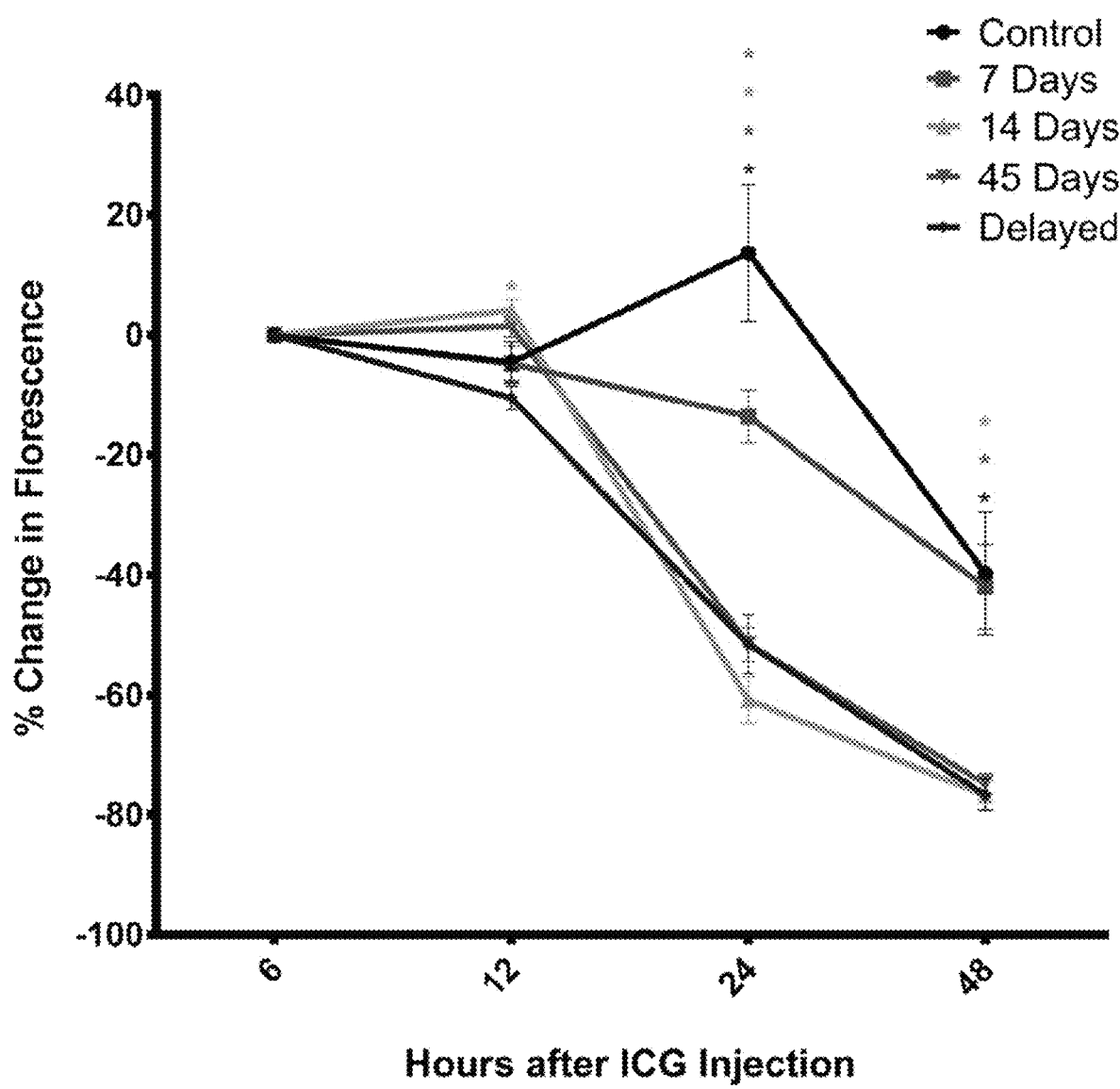

To compare functional lymphatic clearance at the wounded site, the change in fluorescent intensity following indocyanine green (ICG) injection into the distal edge of the tail was quantified. ICG lymphangiography was performed on all animals on day 45 of the experiment. Physiologically, ICG drains from the distal tail proximally, resulting in a washout of contrast and decrease in fluorescent intensity of the tail over time (FIG. 7A). The percent change in fluorescence from immediately after injection was measured at 0, 1, 2, 3, 6, 12, 24, and 48 hours following ICG injection. In all groups, ICG fluorescence peaked 6-hours post-injection and plateaued for 12-hours, showing a subsequent divergence beginning at the $24^{th}$ hour. Specifically, all groups showed a significant decrease in the percent change of fluorescent intensity compared to the control at 24-hours. 48-hours after injection, the 14-day, 42-day and 7-day delayed groups showed a significant decrease in fluorescent intensity, however, the 7-day group was no longer significant from the control at this time point (FIG. 7B).

Figure 8A:
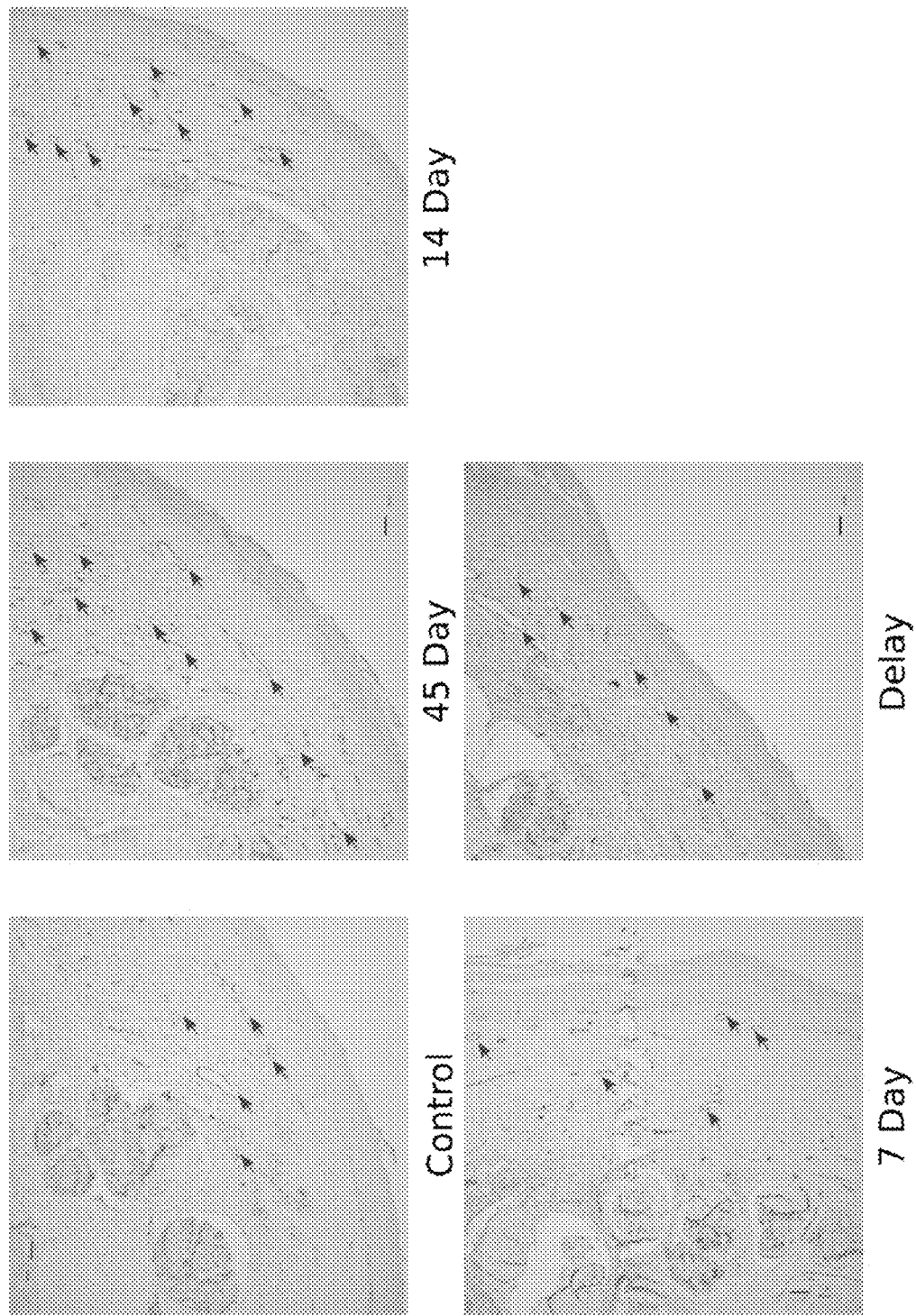
FIGS. 8A and 8B: Lymphatic Vessel Density. (A) Representative cross-sectional 10× immunohistochemistry images of podoplanin+ vessels (stained brown), comparing vessel density of control group to 9-cis RA treated groups. Scale bars: 50 μm. (B) Quantification of lymphatic vessel density for each group. A statistically significant difference was observed between the 45-day group and the vehicle-treated control group (p<0.05); the 14-day group was trending towards significance (p=0.0901). Values reported as mean±standard error.
Figure 8B:
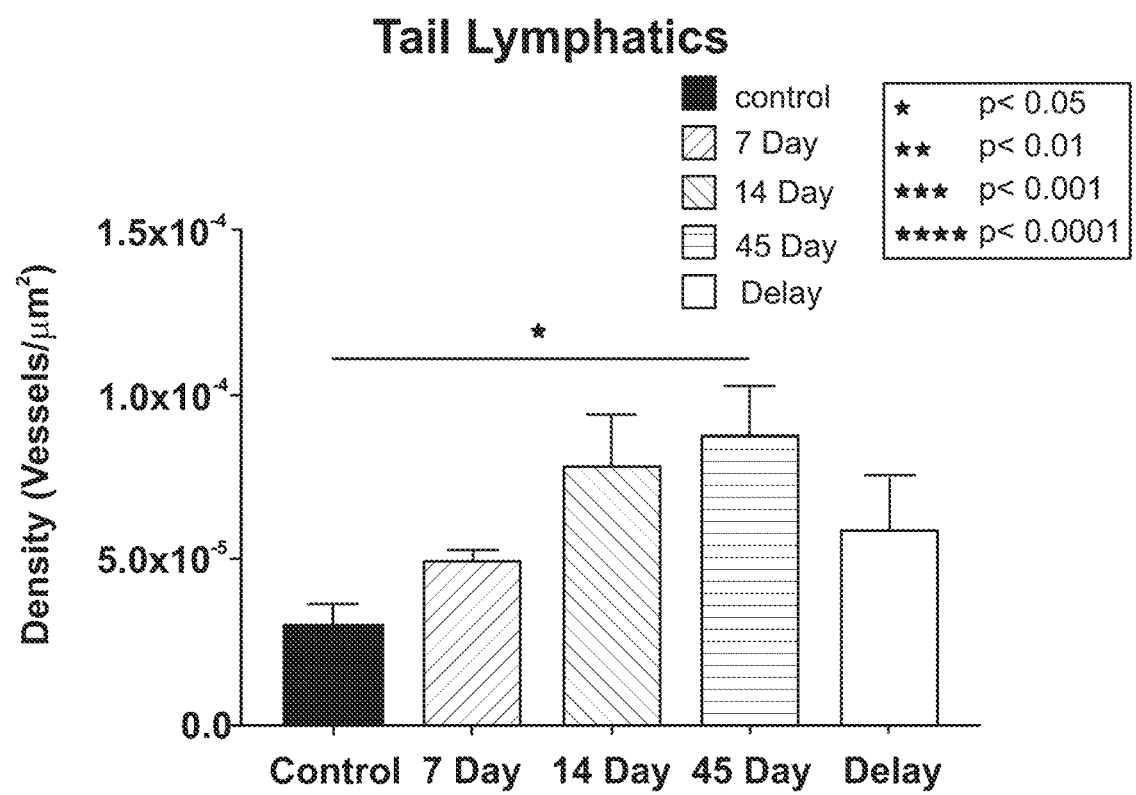

In order to assess the histologic changes after various treatment durations of 9 cis-RA, tails were harvested at the end of the experiment (day 47). Immunohistochemistry analysis of tails distal to the created wounds demonstrated an upwards trend in the lymphatic density with longer durations of therapy, however only the 42-day treatment group was significantly increased compared to the controls ($p<0.05$) (FIG. 8A, 8B).

Figure 9A:
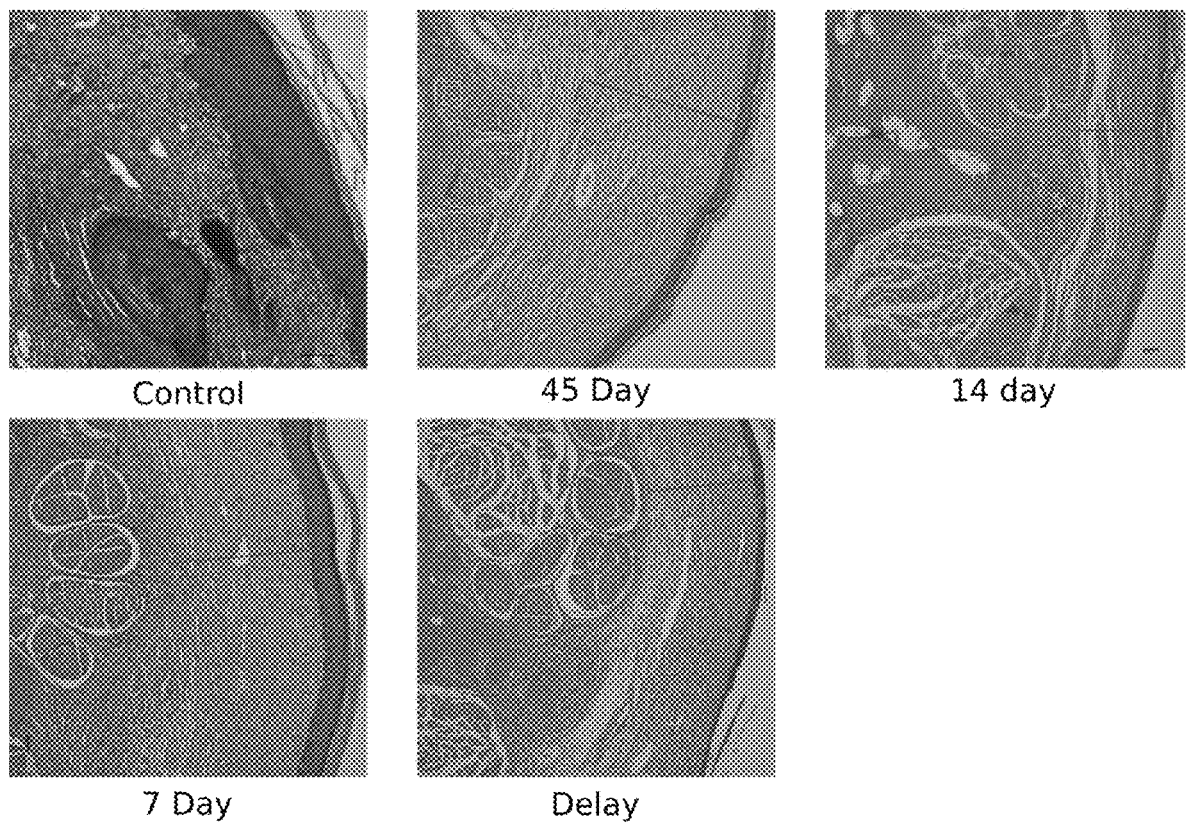
FIGS. 9A and 9B: Dermal and Epidermal Thickness. (A) Representative 10× cross-sectional images of hematoxylin and eosin stained tails. Red indicators represent thickness of dermis (inner lines) and epidermis (outer lines). Scale bar in 14-day group: 50 μm. Scale bar in control group: 100 μm. (b) Quantification of dermal and epidermal thicknesses from H&E stained slides. Control group had a significantly thicker epidermis than the 7-, 14-, 45-day and delay groups (p=0.0411, 0.0001, 0.0001, 0.0001, respectively). The dermis in control tails was also significantly thicker than the 14-, 45-day, and delay groups (p=0.0001, 0.0357, 0.0141, respectively).
Figure 9B:
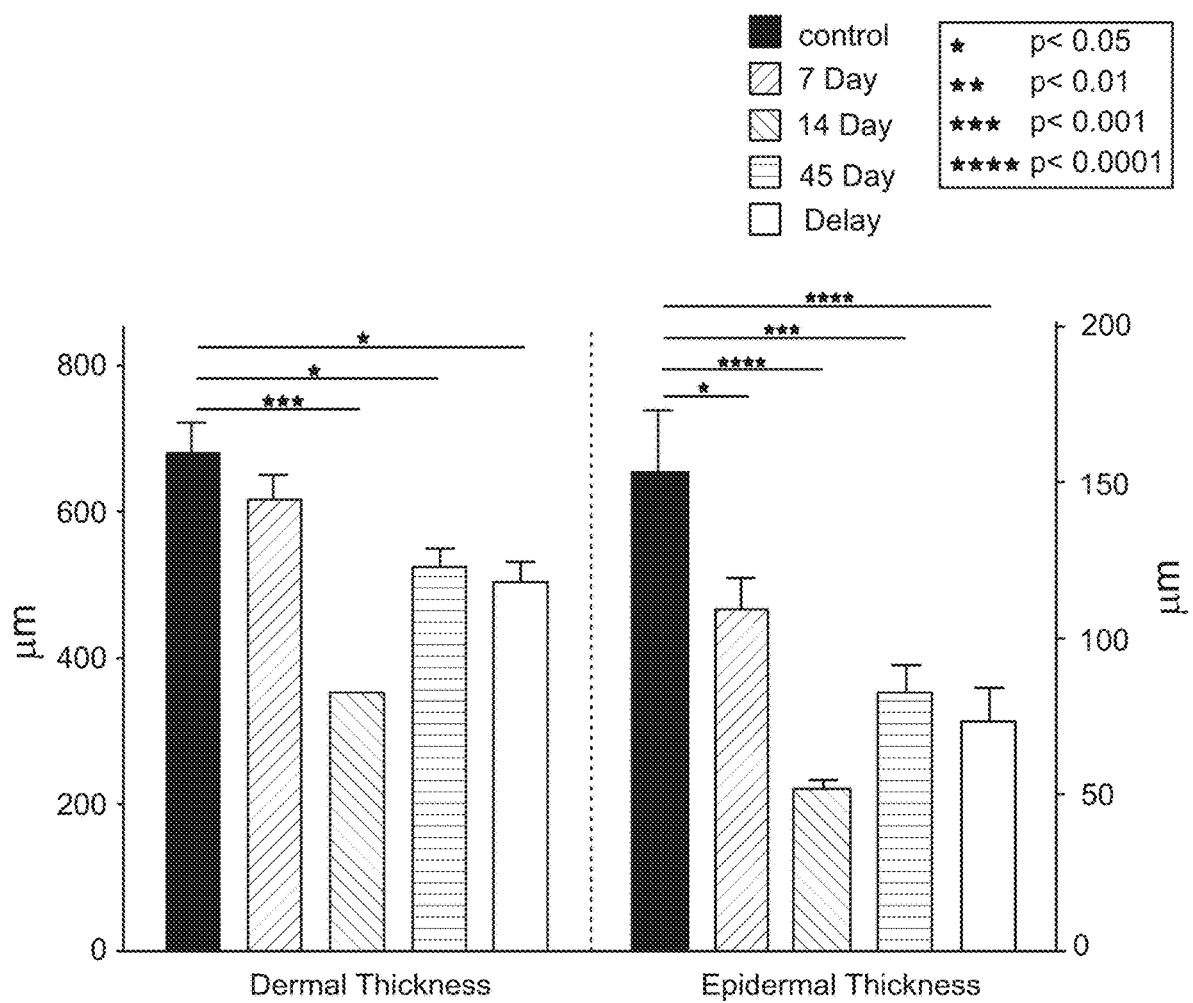

Hematoxylin and eosin (H&E) staining of tail tissue was used to further analyze the effect of 9-cis RA on the histologic manifestations of lymphedema. Dermal thickness was assessed by measuring the distance between the epidermal-dermal junction and the subcutaneous layer. In accordance with the lymphatic density analysis data, animals with prolonged 9-cis RA treatment demonstrated a thinner dermal layer compared to the control (FIG. 9A). Specifically, with the exception of the 7-day treated groups, dermal thickness differed significantly between the control group (679.5±42.12 µm) and the 14-day (352.4±21.29 µm, $p<0.0001$), 45-day (525.2±25.09 µm, $p<0.05$), and delay groups (502±30.17 µm, $P<0.05$) (FIG. 9B). Similarly, the thickness of the epidermis was quantified by measuring the distance between the outer edge of the epidermis and the epidermal-dermal junction. The mean epidermal tail thickness of animals in the control group (153.9±19.83 µm) was significantly greater than all 9-cis RA treated groups including the 7-day group (109.2±10.21 µm, $p<0.05$), 14-day group (52.07±2.616 µm, $p<0.0001$), 45-day group (83.14±8.099 µm, $p<0.001$), and delay group (73.51±10.94 µm, $p<0.0001$) (FIG. 9B).

Figure 10A:
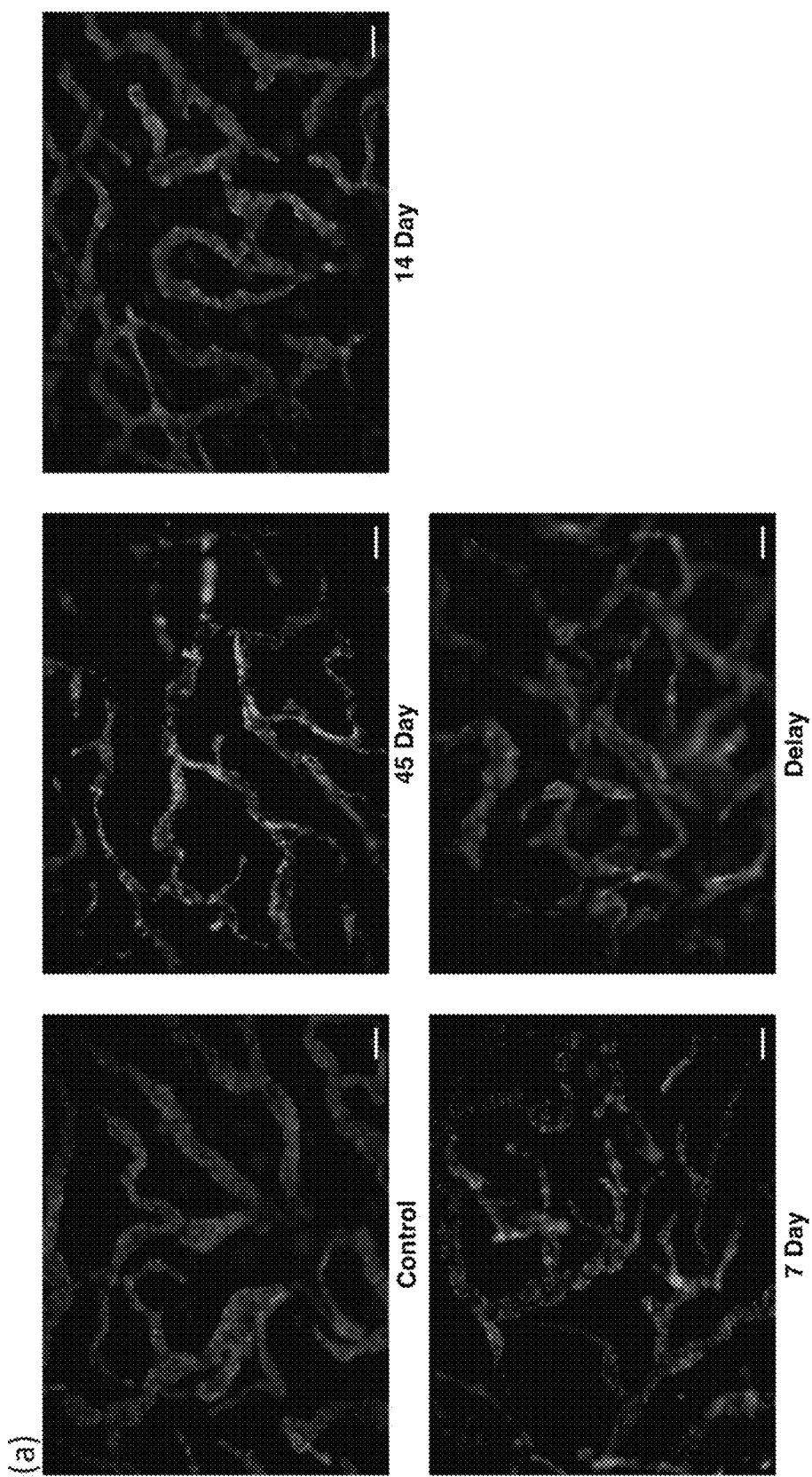
FIGS. 10A and 10B: Lymphatic analysis of distant, uninjured site. (a) Representative images of LYVE-1 stained uninjured ears from mice. Scale bars: 100 μm. (b) Quantification of number of branches, loops, blind-ended sacs, total vessel length, and vessel density. No significant differences were found between the control and treatment groups.
Figure 10B:
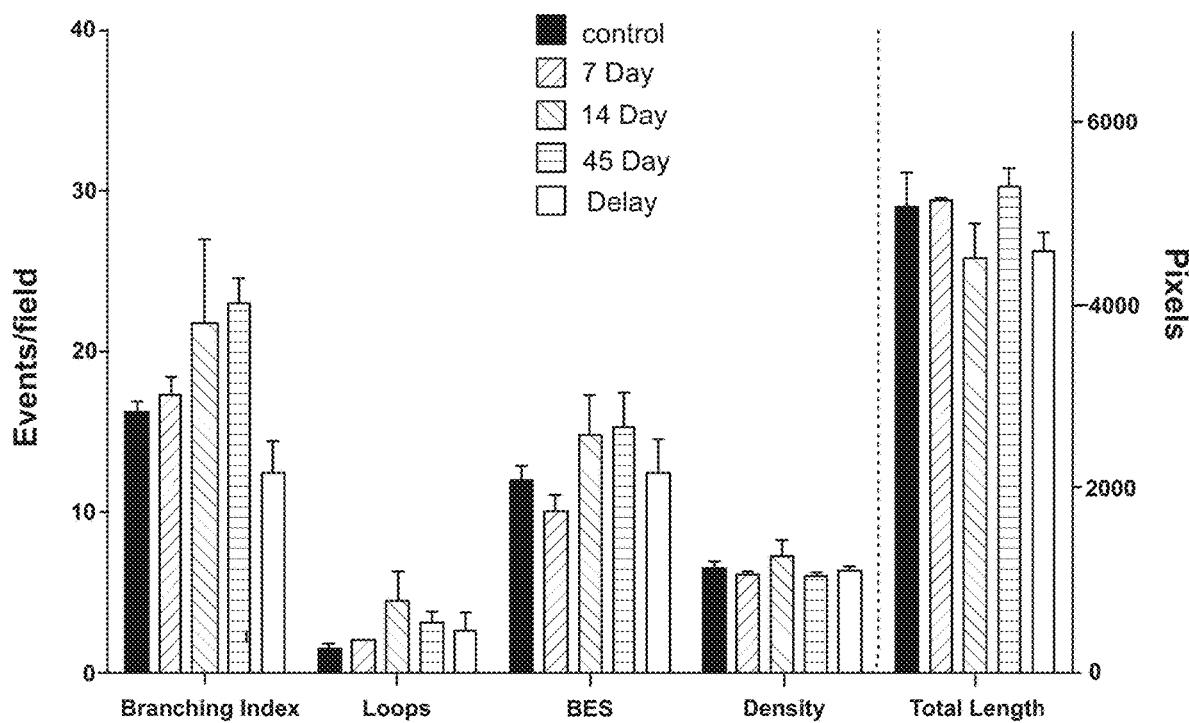
Figure 11A:
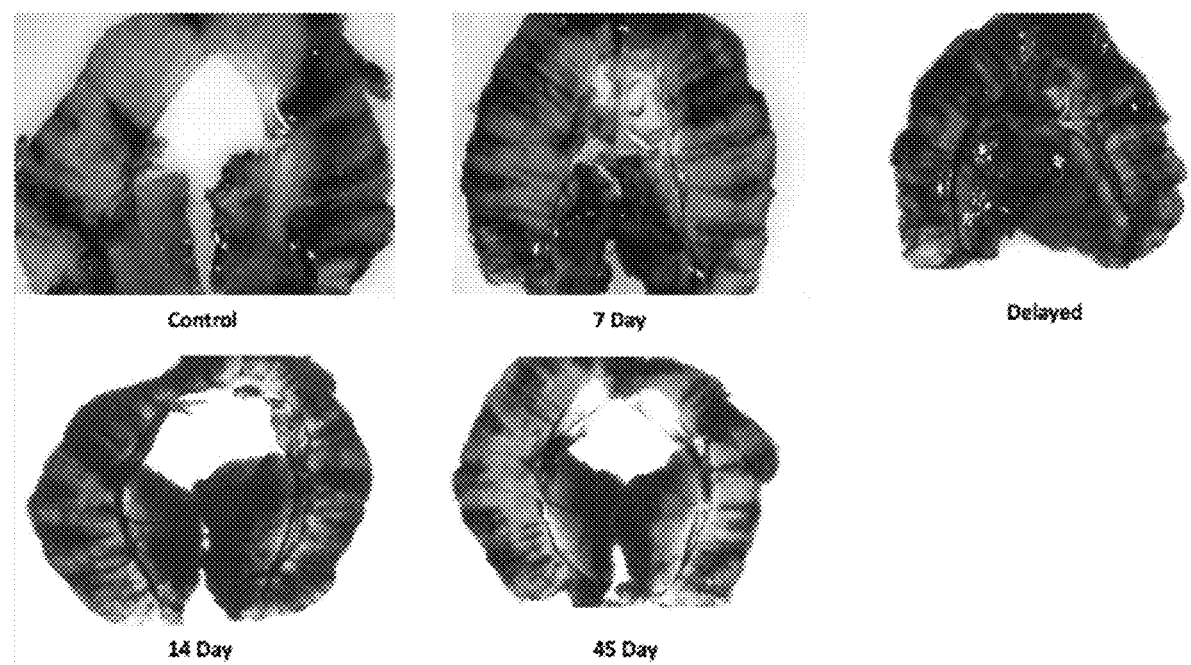
FIGS. 11A and 11B: Lymphatic analysis of India ink stained mouse diaphragms. (A) Representative photos of mouse diaphragms stained with India ink. (B) Graphical representation of the mean percent area stained with India ink. The only statistically significant difference found was between the control group and 14-day group (p=0.0182).
Figure 11B:
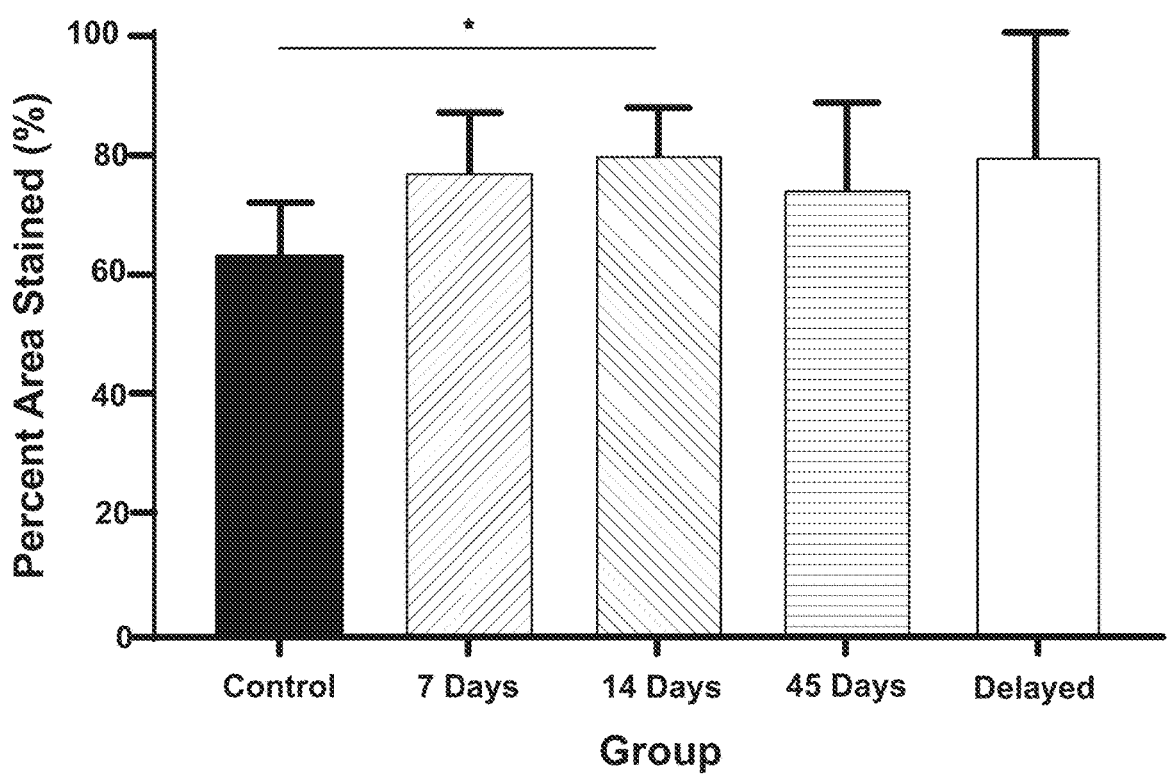

To determine whether 9-cis RA had any effect on lymphatic vessels at sites of uninjured tissue far from the tail injury, whole mount ear preparations were stained for LYVE-1 (immunofluorescence) and quantified (FIG. 10A). Lymphatic vessel analysis of uninjured ears revealed no significant difference in the number of branch points, blind-ended sacs, loops, total length, or density of lymphatic vessels between vehicle-control treated animals and those treated with 9-cis RA for any duration ($p=0.05$) (FIG. 10B). To further analyze the effect of 9-cis RA on the lymphatics of uninjured distant tissue, we utilized the semi-quantitative India ink assay of mice diaphragms. The diaphragm possesses the unique purpose of draining excess intraperitoneal fluid back to the lymphatic system. As such, passive lymphatic uptake of India ink in the peritoneal cavity into the diaphragmatic lymphatics is demonstrative of lymphatic function, with a heavier ink load seen in diaphragmatic tissues with more robust lymphatic networks (FIG. 11A). Quantification of the percent stained area of diaphragms showed that there were essentially no differences with the exception of marginal significance for the 14-day treated group compared to vehicle-treated control animals ($p=0.046$) (FIG. 11B).

Discussion

Lymphedema is a debilitating and disfiguring disease resulting from insufficient lymphatic drainage and subsequent accumulation of lymphatic fluid. Patients commonly present with a combination of swelling and firmness of the affected region, causing symptoms of heaviness, pain, and recurrent infections. Histologic changes seen in lymphedematous tissues include dilated lymphatic vessels, inflammatory cell infiltration, increased thickness of skin and subcutaneous tissue, and increased collagen deposition with fibrosis. Etiologies of this progressive disease are broad and includes congenital, surgical, radiation or infection. However, secondary lymphedema resulting from the surgical treatment of solid tumors is most commonly seen in industrialized countries such as the United States. Despite efforts to create varied approaches for the treatment and prevention of lymphedema, the incidence of this disease has been on the rise from an increase in cancer survivorship and average life expectancy.

9-cis Retinoic Acid (9-cis RA), is an endogenous retinoic acid isoform that has been extensively studied in various disease processes and has shown effective therapeutic potential in conditions ranging from skin diseases to solid organ tumors. Currently, topical 9cis-RA is approved by the FDA for human use Kaposi's sarcoma associated skin lesions and is available in an oral suspension in the United Kingdom for the treatment of refractory eczema. Studies have shown this drug to be generally well tolerated, with a relatively benign side effect profile even with high dose systemic administration. Previously, our group has shown in a murine model that 6 weeks of continuous systemic intraperitoneal 9-cis RA therapy prevents postsurgical lymphedema and is associated with increased lymphatic clearance and lymphangiogenesis. In order to extend our understanding of 9-cis RA in vivo, we set out to explore the minimum effective dosing regimen and effect of delayed administration in our established tail lymphedema model.

Consistent with our previous studies, results from the current study corroborated the efficacy of 9-cis RA treatment in preventing clinical lymphedema, improving lymphatic clearance, and stimulating lymphatic regeneration. Short duration treatment of 9-cis RA for 7 days, had no significant effect on tail lymphedema or dermal thickening. As one might expect, the intermediate 14-day treated group showed more of a response then 7-day treatment but less than that of continuous 45-day treatment. Specifically, the 14-day group showed improved lymphatic function and ICG clearance, decreased dermal and epidermal thickness, and a trend towards increased lymphatic density that did not reach statistical significance (p=0.08) compared to vehicle treated controls. There was no significant difference in tail volume in the 14-day treatment group (Table 1, 2, see FIG. 12).

The association of various other risk factors of lymphedema, including infection, radiation and obesity, suggests that lymphedema is a multifactorial disease whereby lymphatic disruption is necessary but not sufficient for the development of chronic lymphedema. Given the close association of inflammation and lymphedema, we further studied the effects of 9-cis RA on uninjured tissue distant from the experimental wound site. Histologic analysis demonstrated that sites without lymphatic injury or inflammation did not show an appreciable difference in lymphatic regeneration upon 9-cis RA therapy compared to vehicle treated controls. This is an important finding Interestingly, the delayed group that received 7-days of 9-cis RA after one week after lymphatic injury showed a significant improvement in lymphedema with associated decreased tail volume, decreased dermal thickness and improved lymphatic clearance. Overall, the 7-day delay treatment group showed a clinical and histologic response similar to the 14-day treated animals with lymphatic density showing a strong trend towards improvement but not statistical significance (p=0.56) (Table 1, 2). We hypothesize the improved lymphangiogenic effects seen with the delayed short duration 7-day therapy of 9-cis RA, attributable to the intricate interaction of 9-cis RA with a more robust inflammatory cell infiltrate during days 7-14 of the experiment. Lymphangiogenesis serves both as an instigating factor of chronic inflammation as well as a downstream sequelae of inflammation. As a consequence, injured soft tissue with disrupted lymphatic beds are prone to a vicious cycle of an upregulated immune response and activation of the indirect lymphangiogenic pathway. As such, our data reflects on the importance of the timing of 9-cis RA therapy as being tantamount to the duration of treatment in the prevention of clinical lymphedema.

In summary, this series of experiments confirm the efficacy of 9-cis RA in stimulating lymphatic regeneration, improving lymphatic function and ultimately preventing clinical lymphedema in a well-established tail lymphedema model. Given the increasing incidence of lymphedema in an era where primary treatment is mainly limited to palliative therapy without an effective cure, further studies in the development of 9-cis RA as a preventive measure for secondary lymphedema is crucial. In this light, our findings from this study provides strong support that intermediate duration therapy (14-days) of 9-cis RA is sufficient for improving lymphatic function and preventing clinical lymphedema, with the potential to limit side effects of systemic therapy. The ability to translate these findings to human patients at risk for the development of lymphedema will help facilitate finding a preventive solution to this morbid disease.

3. Oral Administration Experiments.

Oral administration experiments were performed on 30 adult BALB/c mice, 12 to 14 weeks old, and weighing between 21 and 30 g. Surgical excision of lymphatic vessels at 20-mm from the base of the tail was performed in order to induce secondary lymphedema. Mice receive 9-cis RA dissolved in sunflower oil via oral gavage for 6 weeks in accordance to the dosing regimes in Table 3.

TABLE 3

Dosing for orally administering 9-cis RA.

| Group | Dosage | Total Volume Administered Orally |
|---|---|---|
| Control | 0 | 0.15 mL |
| Low 9-cis RA | 10 mg/kg | 0.15 mL |
| High 9-cis RA | 30 mg/kg | 0.15 mL |

Figure 13A:
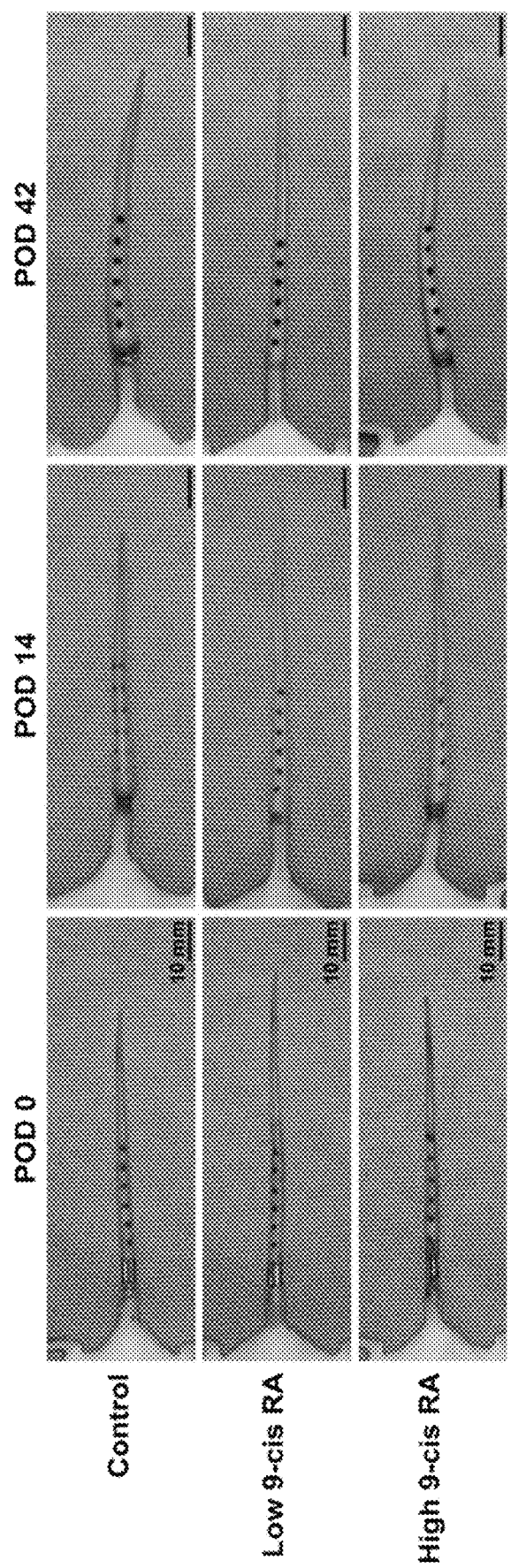
FIGS. 13A, 13B, and 13C: (A) Images showing orally administered 9-cis RA decreases change in gross tail volume. (B) Plots showing orally administered 9-cis RA decreases change in gross tail volume. (C) Plots Orally administered 9-cis RA improves lymphatic clearance.
Figure 13B:
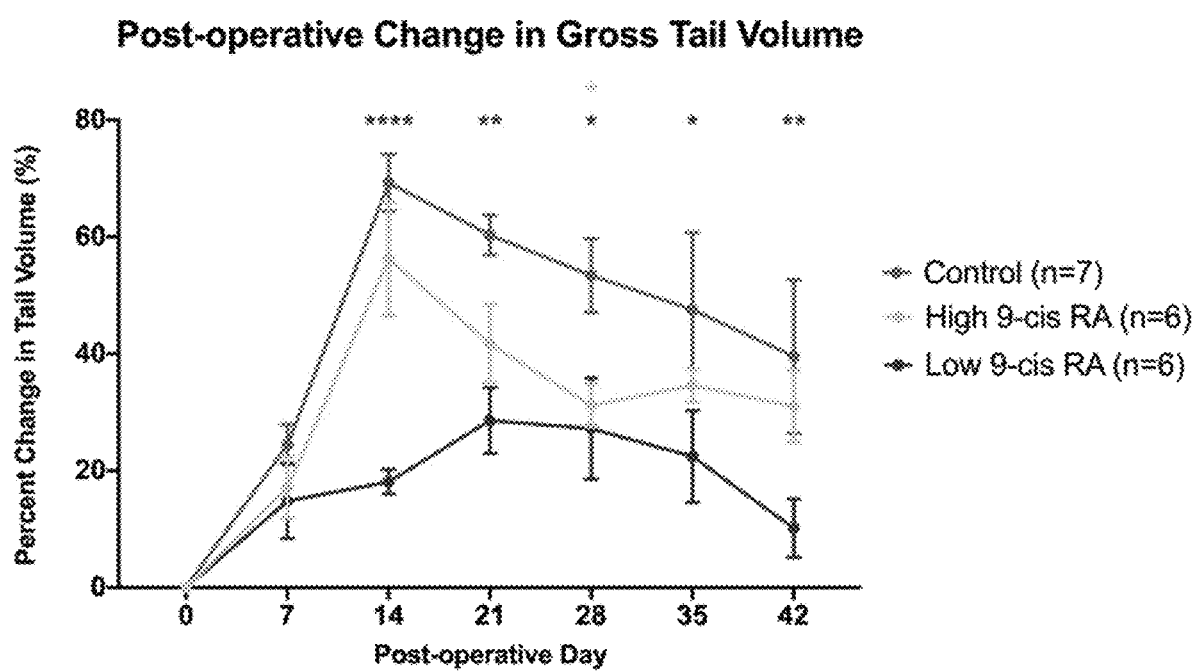
Figure 13C:
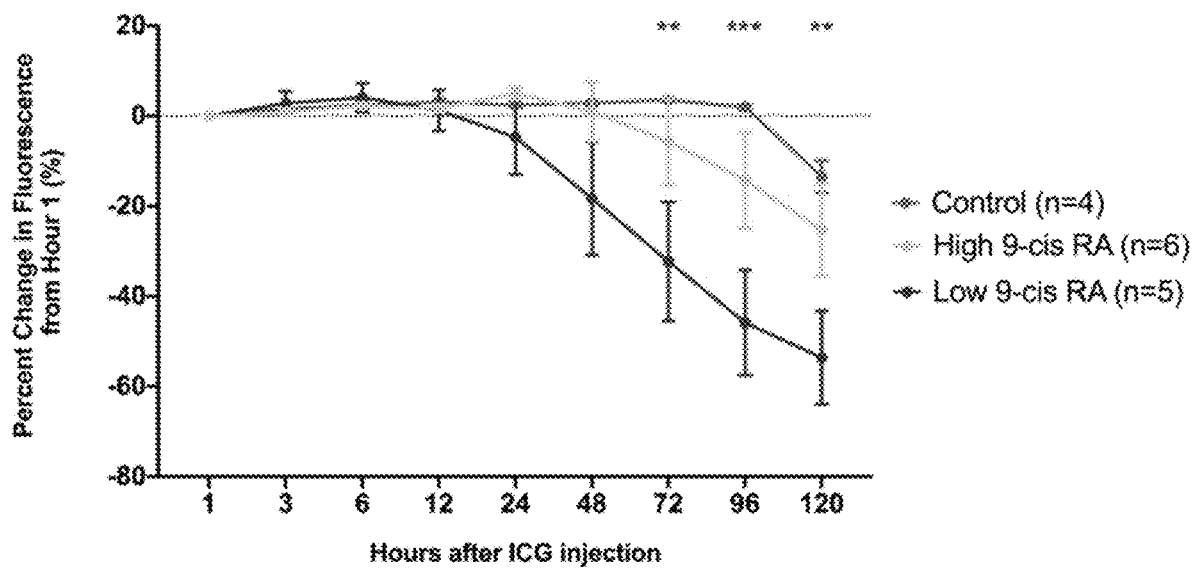

FIG. 13A provides images that show orally administered 9-cis RA decreases change in gross tail volume. FIG. 13B provides plots that show orally administered 9-cis RA decreases change in gross tail volume both at high and low doses. FIG. 13C provides plots that show orally administered 9-cis RA improves lymphatic clearance both at high and low doses. The data supports that a low 10 mg/kg oral dose of 9-cis retinoic acid is most effective for preventing post-surgical tail lymphedema.

Figure 14C:
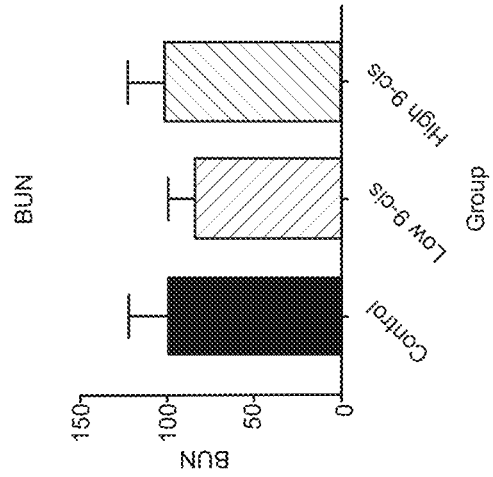
FIGS. 14A, 14B, and 14C: (A) Bar chart showing effect of orally administered 9-cis RA on the liver enzyme AST. (B) Bar chart showing effect of Orally administered 9-cis RA on the liver enzyme ALT. (C). Bar chart showing effect of orally administered 9-cis RA on blood urea nitrogen.
Figure 14B:
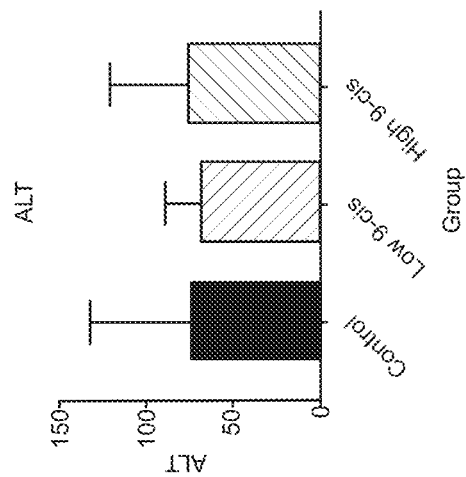
Figure 14A:
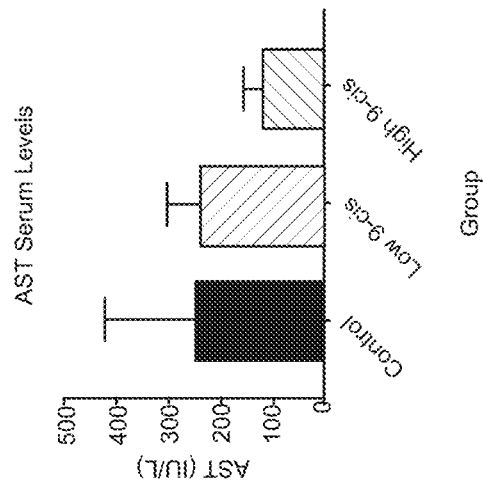

FIG. 14A provides a bar chart showing effect of orally administered 9-cis RA on the liver enzyme AST. FIG. 14B provides a bar chart showing the effect of orally administered 9-cis RA on the liver enzyme ALT. FIG. 14C provides a bar chart showing effect of orally administered 9-cis RA on blood urea nitrogen (kidney function test). These results show that both the high and low doses of RA have minimal systemic toxicity as measured by liver and kidney function tests.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

1. Schulze H, Nacke M, Gutenbrunner C, Hadamitzky C (2018) Worldwide assessment of healthcare personnel dealing with lymphoedema. Health Econ Rev 8: 10.
2. Rockson S G, Rivera K K (2008) Estimating the population burden of lymphedema. Ann N Y Acad Sci 1131: 147-154.
3. Shih Y C, Xu Y, Cormier J N, Giordano S, Ridner S H, et al. (2009) Incidence, treatment costs, and complications of lymphedema after breast cancer among women of working age: a 2-year follow-up study. J Clin Oncol 27: 2007-2014.

4. Dellon A L, Hoopes J E (1977) The Charles procedure for primary lymphedema. Long-term clinical results. Plast Reconstr Surg 60: 589-595.
5. Szuba A, Skobe M, Karkkainen M J, Shin W S, Beynet D P, et al. (2002) Therapeutic lymphangiogenesis with human recombinant VEGF-C. FASEB J 16: 1985-1987.
6. Honkonen K M, Visuri M T, Tervala T V, Halonen P J, Koivisto M, et al. (2013) Lymph node transfer and perinodal lymphatic growth factor treatment for lymphedema. Ann Surg 257: 961-967.
7. Tammela T, Saaristo A, Holopainen T, Lyytikka J, Kotronen A, et al. (2007) Therapeutic differentiation and maturation of lymphatic vessels after lymph node dissection and transplantation. Nat Med 13: 1458-1466.
8. Jin D P, An A, Liu J, Nakamura K, Rockson S G (2009) Therapeutic responses to exogenous VEGF-C administration in experimental lymphedema: immunohistochemical and molecular characterization. Lymphat Res Biol 7: 47-57.
9. Skobe M, Hawighorst T, Jackson D G, Prevo R, Janes L, et al. (2001) Induction of tumor lymphangiogenesis by VEGF-C promotes breast cancer metastasis. Nat Med 7: 192-198.
10. Cao R, Ji H, Feng N, Zhang Y, Yang X, et al. (2012) Collaborative interplay between FGF-2 and VEGF-C promotes lymphangiogenesis and metastasis. Proc Natl Acad Sci USA 109: 15894-15899.
11. Peppicelli S, Bianchini F, Calorini L (2014) Inflammatory cytokines induce vascular endothelial growth factor-C expression in melanoma-associated macrophages and stimulate melanoma lymph node metastasis. Oncol Lett 8: 1133-1138.
12. Choi I, Lee S, Kyoung Chung H, Suk Lee Y, Eui Kim K, et al. (2012) 9-cis retinoic acid promotes lymphangiogenesis and enhances lymphatic vessel regeneration: therapeutic implications of 9-cis retinoic acid for secondary lymphedema. Circulation 125: 872-882.
13. Bramos A, Perrault D, Yang S, Jung E, Hong Y K, et al. (2016) Prevention of Postsurgical Lymphedema by 9-cis Retinoic Acid. Ann Surg 264: 353-361.
14. Choi I, Chung H K, Ramu S, Lee H N, Kim K E, et al. (2011) Visualization of lymphatic vessels by Prox1-promoter directed GFP reporter in a bacterial artificial chromosome-based transgenic mouse. Blood 117: 362-365.
15. Williams A F, Franks P J, Moffatt C J (2005) Lymphoedema: estimating the size of the problem. Palliat Med 19: 300-313.
16. Moffatt C J, Franks P J, Doherty D C, Williams A F, Badger C, et al. (2003) Lymphoedema: an underestimated health problem. QJM 96: 731-738.
17. Greene A K, Borud L J, Slavin S A (2010) Lymphedema. Plastic Surgery Secrets Plus. Second ed: Mosby. pp. 630-635.

What is claimed is:

1. A method of treating post-surgical edema, the method comprising:
identifying a subject undergoing surgery that is at risk for edema; and
administering an effective amount of a pharmaceutical composition to the subject, the pharmaceutic composition including a retinoic acid component selected from the group consisting of 9-cis retinoic acid, geometric isomers of 9-cis retinoic acid, metabolites of 9-cis retinoic acid, substituted derivatives thereof, and combinations thereof, wherein a dosage of the retinoic acid component for a human subject is 0.001 mg to 50 mg per kg of subject weight and wherein the dosage is administered over a time period of 15 to 90 days.

2. The method of claim 1 wherein the subject is identified for being at risk for post-surgical lymphedema.

3. The method of claim 1 wherein the subject is identified for being at risk for general edema following surgery.

4. The method of claim 1 wherein the pharmaceutical composition is administered orally, intravenously, by implant, liposomally, intranasally, topically, rectally, by a transdermal patch, or parentally.

5. The method of claim 1 wherein the pharmaceutical composition further includes one or more diluents, excipients, and carriers.

6. The method of claim 1 wherein the pharmaceutical composition is administered by implanting an implantable pellet into the subject during or after surgery, the implantable pellet including a carrier and the retinoic acid component dispersed within the carrier in an effective amount to treat postsurgical lymphedema.

7. The method of claim 6 wherein the 9-cis retinoic acid is present in an amount of 0.5 to 10 milligrams per kg of subject weight.

8. The method of claim 6 wherein the carrier is at least partially biodegradable.

9. The method of claim 6 wherein the carrier is a biodegradable matrix that effectively and continuously releases 9-cis retinoic acid when the implantable pellet is implanted in a subject.

10. The method of claim 9 wherein at least 90 percent of the 9-cis retinoic acid is released into the subject for 60 days post implantation.

11. The method of claim 9 wherein the carrier includes cholesterol, lactose, celluloses, phosphates, and stearates.

12. The method of claim 1 wherein the 9-cis retinoic acid is provided in a sustained release formulation.

13. The method of claim 1 wherein the pharmaceutical composition is administered orally.

14. A method of treating post-surgical edema, the method comprising:
identifying a subject undergoing surgery that is at risk for edema; and
administering an effective amount of a pharmaceutical composition to the subject, the pharmaceutic composition including a retinoic acid component selected from the group consisting of 9-cis retinoic acid, geometric isomers of 9-cis retinoic acid, metabolites of 9-cis retinoic acid, substituted derivatives thereof, and combinations thereof, wherein the pharmaceutical composition is administered orally, intravenously, by implant, liposomally, intranasally, topically, rectally, by a transdermal patch, or parentally.

15. The method of claim 14, wherein the subject is identified for being at risk for post-surgical lymphedema.

16. The method of claim 14, wherein the subject is identified for being at risk for general edema following surgery.

17. The method of claim 14, wherein a dosage of the retinoic acid component for a human subject is 0.001 mg to 50 mg per kg of subject weight.

18. The method of claim 17 wherein the dosage is administered over a time period of 15 to 90 days.

19. The method of claim 14, wherein the pharmaceutical composition further includes one or more diluents, excipients, and carriers.

20. A method of treating post-surgical edema, the method comprising:

identifying a subject undergoing surgery that is at risk for edema; and administering an effective amount of a pharmaceutical composition to the subject, the pharmaceutic composition including a retinoic acid component selected from the group consisting of 9-cis retinoic acid, geometric isomers of 9-cis retinoic acid, metabolites of 9-cis retinoic acid, substituted derivatives thereof, and combinations thereof, wherein the pharmaceutical composition is administered by implanting an implantable pellet into the subject during or after surgery, the implantable pellet including a carrier and the retinoic acid component dispersed within the carrier in an effective amount to treat postsurgical lymphedema.

21. The method of claim 20, wherein the 9-cis retinoic acid is present in an amount of 0.5 to 10 milligrams per kg of subject weight.

22. The method of claim 20, wherein the carrier is at least partially biodegradable.

23. The method of claim 20, wherein the carrier is a biodegradable matrix that effectively and continuously releases 9-cis retinoic acid when the implantable pellet is implanted in a subject.

24. The method of claim 23, wherein at least 90 percent of the 9-cis retinoic acid is released into the subject for 60 days post implantation.

25. The method of claim 23, wherein the carrier includes cholesterol, lactose, celluloses, phosphates, and stearates.

26. The method of claim 20, wherein the 9-cis retinoic acid is provided in a sustained release formulation.

* * * * *